(12) United States Patent
Yocum et al.

(10) Patent No.: US 10,041,094 B2
(45) Date of Patent: Aug. 7, 2018

(54) FERMENTATION OF GLYCEROL TO ORGANIC ACIDS

(75) Inventors: R. Rogers Yocum, Lexington, MA (US); Theron Hermann, Arlington, MA (US); Xiaohui Hu, Woburn, MA (US)

(73) Assignee: Myriant Corporation, Woburn, MA (US)

( * ) Notice: Subject to any disclaimer, the term of this patent is extended or adjusted under 35 U.S.C. 154(b) by 102 days.

(21) Appl. No.: 14/233,830

(22) PCT Filed: Jul. 22, 2011

(86) PCT No.: PCT/US2011/045001
§ 371 (c)(1),
(2), (4) Date: Apr. 23, 2014

(87) PCT Pub. No.: WO2013/015770
PCT Pub. Date: Jan. 31, 2013

(65) Prior Publication Data
US 2014/0234923 A1     Aug. 21, 2014

(51) Int. Cl.
| | |
|---|---|
| C12P 7/46 | (2006.01) |
| C12N 1/20 | (2006.01) |
| C12N 15/52 | (2006.01) |
| C07K 14/245 | (2006.01) |
| C12N 9/04 | (2006.01) |
| C12N 9/12 | (2006.01) |
| C12P 7/56 | (2006.01) |

(52) U.S. Cl.
CPC .............. *C12P 7/46* (2013.01); *C07K 14/245* (2013.01); *C12N 1/20* (2013.01); *C12N 9/0006* (2013.01); *C12N 9/1205* (2013.01); *C12N 15/52* (2013.01); *C12P 7/56* (2013.01); *C12Y 101/01008* (2013.01); *C12Y 101/05003* (2013.01)

(58) Field of Classification Search
None
See application file for complete search history.

(56) References Cited

U.S. PATENT DOCUMENTS

| | | |
|---|---|---|
| 5,000,000 A | 3/1991 | Ingram |
| 5,028,539 A | 7/1991 | Ingram |
| 5,424,202 A | 6/1995 | Ingram |
| 5,482,846 A | 1/1996 | Ingram |
| 5,916,787 A | 6/1999 | Ingram |

(Continued)

FOREIGN PATENT DOCUMENTS

| | | |
|---|---|---|
| KR | 20100092190 | 12/2011 |
| WO | 2007115228 A3 | 10/2007 |

(Continued)

OTHER PUBLICATIONS

GenBank Accession No. ABE09922.1, published Apr. 30, 2010.*

(Continued)

*Primary Examiner* — Richard C Ekstrom
(74) *Attorney, Agent, or Firm* — Adam P. Lerner

(57) ABSTRACT

The present invention is in the field of producing organic acids and other useful chemicals via biological fermentation using glycerol as a source of carbon. Novel microorganisms and fermentation processes are described that are capable of converting glycerol to useful organic acids in high yield and high purity.

7 Claims, 6 Drawing Sheets

(56) References Cited

U.S. PATENT DOCUMENTS

| | | | |
|---|---|---|---|
| 6,849,439 | B2 | 2/2005 | Henson |
| 7,098,009 | B2 | 8/2006 | Shanmugham |
| 7,223,567 | B2 | 5/2007 | Ka-Yiu |
| 7,241,594 | B2 | 7/2007 | Lee |
| 7,244,610 | B2 | 7/2007 | San |
| 7,262,046 | B2 | 8/2007 | Ka-Yiu |
| 7,470,530 | B2 | 12/2008 | Lee |
| 7,629,162 | B2 | 12/2009 | Zhou |
| 7,790,416 | B2 | 9/2010 | San |
| 2009/0148914 | A1 | 6/2009 | Causey |
| 2009/0176285 | A1 | 7/2009 | Burd |
| 2009/0186392 | A1 | 7/2009 | Gonzalez |
| 2009/0317876 | A1* | 12/2009 | Rybak et al. ............ 435/107 |
| 2009/0325243 | A1 | 12/2009 | Park |
| 2010/0184171 | A1 | 7/2010 | Jantama |

FOREIGN PATENT DOCUMENTS

| | | |
|---|---|---|
| WO | 2008115958 A2 | 9/2008 |
| WO | 2009024294 A1 | 2/2009 |
| WO | 2010051324 A1 | 5/2010 |
| WO | 2010/092155 A1 | 8/2010 |
| WO | 2010/115067 A1 | 10/2010 |
| WO | WO 2011030204 A1 * | 3/2011 |
| WO | 2009048202 A1 | 4/2015 |

OTHER PUBLICATIONS

Baba, T. et al. "Construction of *Escherichia coli* K-12 in frame, single-gene knockout mutants: the Keio Collection" Molecular Systems Biology, 2006, pp. 1-11, Article No. 2006-0008.

Bell, R. M. "Mutants of *Escherichia coli* defective in membrane phospholipid synthesis: macromolecular synthesis in an sn-glycerol 3-phosphate aceyltransferase Km mutant" Journal of Bacteriology, 1974, pp. 1065-1076, vol. 117.

Berman, M, et al. "Glycerol-specific revertants of a phosphoenolpyruvate phosphotransferase mutant: suppression by the desensitization of glycerol kinase to feedback inhibition" Journal of Bacteriology, 1971, pp. 113-120, vol. 105.

Blankschien, M.D. et al. "Metabolic engineering of *Escherichia coli* for the production of succinate from glycerol" Metabolic Engineering, 2010, pp. 409-419, vol. 12.

Chen, Z. et al. "Elementary mode analysis for the rational design of efficient succinate conversion from glycerol by *Escherichia coli*" Journal of Biomedicine and Biotechnology, 2010, pp. 1-14, Article ID. 518743.

Clomburg, J. M. et al."Biofuel production in *Escherichia coli*: the role of metabolic engineering and synthetic biology" Applied Microbiology and Biotechnology, 2010, pp. 419-434, vol. 86.

Clomburg, J. M. et al. "Metabolic engineering of *Escherichia coli* for the production of 1,2-propanediol from glycerol" Biotechnology and Bioengineering, 2010, pp. 867-879, vol. 108.

Cronan, J. E. Jr. et al. "Mutants of *Escherichia coli* defective in membrane phospholipid synthesis: mapping of the structural gene for L-glycerol 3-phosphate dehydrogenase" Journal of Bacteriology, 1974, pp. 598-605, vol. 118.

Cronan, J.E. Jr. et al. "Mutants of *Escherichia col* defective in membrane phospholipid synthesis: Mapping of sn-glycerol 3-phosphate acyltransferase Km mutants" Journal of Bacteriology, 1974, pp. 227-233, vol. 120.

Datsenko K.A. et al. "one-step inactivation of chromosomal genes in *Escherichia coli* K-12 using PCR products" Proceedings of National Academy of Sciences USA, 2000, pp. 6640-6645, vol. 97.

Durnin, G. et al. "Understanding and harnessing the microaerobic metabolism of glycerol in *Escherichia coli*" Biotechnology and Bioengineering, 2009, pp. 148-161, vol. 103.

Gonzalez, et al. "A new model for the anaerobic fermentation of lgycerol in entric bacteria: trunk and auxiliary pathways in *Escherichia coli*" Metabolic Engineering, 2008, pp. 234-245, vol. 10.

Herriing, C.D. et al. "Comparative genome sequencing of *Escherchia coli* allows observation of bacterial evolution on a laboratory time scale" Nature Genetics, 2006, pp. 1406-1412, vol. 38.

Honisch, C. et al. "High-throughput mutation detection underlying adaptive evolution of *Escherichia coli* K12" Genome Research, 2004, pp. 2495-2502, vol. 14.

Jantama, K. et al. "combining metabolic engineering and metabolic evolution to develop nonrecombinant strains of *Escherichia coli* C that produce succinate and malate" Biotechnology and Bioengineering, 2008, pp. 1140-1153, vol. 99.

Jantama, K. et al. "Eliminating side products and increasing succinic acid yield in engineered strains of *Escherichia coli* C" Biotechnology and Bioengineering, 2008, pp. 881-893, vol. 101.

Ibarra, R. U. et al. "*Escherichia coli* K-12 undergoes adaptive evolution to achieve in silico predicted optimal growth" Nature, 2002, pp. 186-189, vol. 420.

Pettigrew, D. W. et al. "A single amino acid change in *Escherichia coli* glycerol kinase abolishes glucose control of glycerol utilization in vivo" Journal of Bacteriology 1996, pp. 2846-2852, vol. 178.

Trinh, C. T. et al. "Metabolic engineering of *Escherichia coli* for efficient conversion of glycerol to ethanol" Applied and Environmental Microbiology, 2009, pp. 6696-6705, vol. 75.

Yazdani, S.S. et al. "Anaerobic fermentation of glycerol: a path to economic viability for the biofules industry" Current Opinion in Biotechnology, 2007, pp. 213-219, vol. 18.

Yazdani, S. et al. "Engineering *Escherichia coli* for the efficient conversion of glycerol to ethanol and co-products" Metabolic Engineering, 2008, pp. 340-351, vol. 10.

Zhang, X. et al. "Metabolic evolution of energy-conserving pathways for succinic acid production in *Escherichia coli*" Proceedings of National Academy of Sciences USA, 2009, pp. 20180-20185, vol. 106.

Zhang, X. et al. "Reengineering *Escherichia coli* for succinate production in mineral salts medium" Applied and Environmental Microbiology, 2009, pp. 7807-7813, vol. 75.

Zhang, X. et al. "Fermentationof glycerol to succinate by metabolically engineered strains of *Escherichia coli*" Applied and Environmental Microbiology, 2010, pp. 2397-2401, vol. 76.

Zwaig, N. et al. "Feedback inhibition of glycerol kinase, a catabolic enzyme in *Escherichia coli*" Science, 1966, pp. 755-757, vol. 153.

Zwaig, N. et al. "Glycerol kinase, the pacemaker for the dissimilation of glycerol in *Escherichia coli*" Journal of Bacteriology, 1970, pp. 753-759, vol. 102.

Lin, E. C. "Dissimilatory pathways for sugars polyols and carbohydrates" *Escherichia coli* and *Salmonella*: Cellular and molecular biology, 1996, pp. 307-342, ASM Press, Washington D. C.

Holtman, C. K. et al. "Reverse genetics of *Escherichia coli* glycerol kinase allosteric regulation and glucose control of glycerol utilization in vivo" Journal of Microbiology, 2001, pp. 3336-3344, vol. 183.

Mazumdar, S. et al. "*Escherichia coli* strains engineered for homofermentattive production of D-lactic acid from glycerol" Applied and Environmental Microbiology, 2010, pp. 4327-4336, vol. 76.

Rittmann, D. et al. "Engineering of a glycerol utilization pathway for amino acid production by Corynebacterium glutamicum" Applied and Environmental Microbiology, 2008, pp. 6216-6222, vol. 74.

Murarka, A. et al. "Fermentative utilization of glycerol by *Escherichia coli* and its implications for the production of fuels and chemicals" Applied and Environmental Microbiology, 2008, pp. 1124-1135, vol. 74.

Palsson, B. O. "Adaptive laboratory evolution" Microbe, 2011, pp. 69-74, vol. 6.

\* cited by examiner

SEQUENCE LISTING

<160> NUMBER OF SEQ ID NOS: 11

<210> SEQ ID NO 1
<211> LENGTH: 19
<212> TYPE: DNA
<213> ORGANISM: Artificial Sequence
<220> FEATURE:
<223> OTHER INFORMATION: PCR Primer BY19

<400> SEQUENCE: 1
tccggcgcgc caccaatac                                                19

<210> SEQ ID NO 2
<211> LENGTH: 23
<212> TYPE: DNA
<213> ORGANISM: Artificial Sequence
<220> FEATURE:
<223> OTHER INFORMATION: PCR Primer BY44

<400> SEQUENCE: 2
cagtgtcatt tggggactgg ggg                                           23

<210> SEQ ID NO 3
<211> LENGTH: 27
<212> TYPE: DNA
<213> ORGANISM: Artificial Sequence
<220> FEATURE:
<223> OTHER INFORMATION: PCR Primer BY15

<400> SEQUENCE: 3
gtatacggtc agactaacat tggcggc                                       27

<210> SEQ ID NO 4
<211> LENGTH: 26
<212> TYPE: DNA
<213> ORGANISM: Artificial Sequence
<220> FEATURE:
<223> OTHER INFORMATION: PCR Primer BY16

<400> SEQUENCE: 4
cgccagtgtt catcagcata aagcag                                        26

<210> SEQ ID NO 5
<211> LENGTH: 28
<212> TYPE: DNA
<213> ORGANISM: Artificial Sequence
<220> FEATURE:
<223> OTHER INFORMATION: PCR Primer BY30

<400> SEQUENCE: 5
atcagctttc gccagcactt ctaccagc                                      28

<210> SEQ ID NO 6
<211> LENGTH: 76

```
<212> TYPE: DNA
<213> ORGANISM: Artificial Sequence
<220> FEATURE:
<223> OTHER INFORMATION: PCR Primer BY71

<400> SEQUENCE: 6
acttttgctt ccagtttctc aaacacttct aatgacattg tcatacctct gtgacggaag    60
atcacttcgc agaata                                                    76

<210> SEQ ID NO 7
<211> LENGTH: 76
<212> TYPE: DNA
<213> ORGANISM: Artificial Sequence
<220> FEATURE:
<223> OTHER INFORMATION: PCR Primer BY72

<400> SEQUENCE: 7
acgatatatt ttttttcagt catgtttaat tgtcccgtag tcatattaca tgaagcactt    60
cactgacacc ctcatc                                                    76

<210> SEQ ID NO 8
<211> LENGTH: 26
<212> TYPE: DNA
<213> ORGANISM: Artificial Sequence
<220> FEATURE:
<223> OTHER INFORMATION: PCR Primer BY73

<400> SEQUENCE: 8
caacctggtt ttgggtagat ttgctc                                         26

<210> SEQ ID NO 9
<211> LENGTH: 29
<212> TYPE: DNA
<213> ORGANISM: Artificial Sequence
<220> FEATURE:
<223> OTHER INFORMATION: PCR Primer BY74

<400> SEQUENCE: 9
acagtaaaga aattacgcgg aagatgaag                                      29

<210> SEQ ID NO 10
<211> LENGTH: 2133
<212> TYPE: DNA
<213> ORGANISM: Escherichia coli
<220> FEATURE:
<221> NAME/KEY: misc_feature
<223> OTHER INFORMATION: pRY521 Plasmid.  Parent of pMH4 series of
      palsmid

<400> SEQUENCE: 10
ccaatacgca aaccgcctct ccccgcgcgt tggccgattc attaatgcag ctggcacgac    60
aggtttcccg actggaaagc gggcagtgag cgcaacgcaa ttaatgtgag ttagctcact   120
cattaggcac cccaggcttt acactttatg cttccggctc gtatgttgtg tggaattgtg   180
agcggataac aatttcacac aggaaacagc tatgaccatg attacgccaa gctatttagg   240
tgacactata gaatactcaa gctatgcatc caacgcgttg ggagctctcc catatggtcg   300
acctgcaggc ggccgcacta gtgatatccc gcggccatgg cggccgggag catgcgacgt   360
cgggcccaat tcgccctata gtgagtcgta ttacaattca ctggccgtcg ttttacaacg   420
tcgtgactgg gaaaaccctg gcgttaccca acttaatcgc cttgcagcac atccccctt    480 cgccagctgg cgtaatagcg aagaggcccg caccgatcgc ccttcccaac agttgcgcag   540
```

```
cctgaatggc gaatgagctt gcgccgtccc gtcaagtcag cgtaatgctc tgccagtgtt      600
acaaccaatt aaccaattct gattagaaaa actcatcgag catcaaatga aactgcaatt      660
tattcatatc aggattatca ataccatatt tttgaaaaag ccgtttctgt aatgaaggag      720
aaaactcacc gaggcagttc cataggatgg caagatcctg gtatcggtct gcgattccga      780
ctcgtccaac atcaatacaa cctattaatt tcccctcgtc aaaaataagg ttatcaagtg      840
agaaatcacc atgagtgacg actgaatccg gtgagaatgg caaaaggtta tgcatttctt      900
tccagacttg ttcaacaggc cagccattac gctcgtcatc aaaatcactc gcatcaacca      960
aaccgttatt cattcgtgat tgcgcctgag cgagacgaaa tacgcgatcg ctgttaaaag     1020
gacaattaca acaggaatc gaatgcaacc ggcgcaggaa cactgccagc gcatcaacaa     1080
tattttcacc tgaatcagga tattcttcta atacctggaa tgctgttttc ccagggatcg     1140
cagtggtgag taaccatgca tcatcaggag tacggataaa atgcttgatg gtcggaagag     1200
gcataaattc cgtcagccag tttagtctga ccatctcatc tgtaacatca ttggcaacgc     1260
tacctttgcc atgtttcaga aacaactctg gcgcatcggg cttcccatac aatcaataga     1320
ttgtcgcacc tgattgcccg acattatcgc gagcccattt atacccatat aaatcagcat     1380
ccatgttgga atttaatcgc ggcctcgacg agcaagacgt ttcccgttga atatggctca     1440
taacacccct tgtattactg tttatgtaag cagacagttt tattgttcat gatgatatat     1500
ttttatcttg tgcaatgtaa catcagagat tttgagacac tcgacaagat gatcttcttg     1560
agatcgtttt ggtctgcgcg taatctcttg ctctgaaaac gaaaaaaccg ccttgcaggg     1620 cggttttttcg aaggttctct gagctaccaa ctctttgaac cgaggtaact ggcttggagg     1680
agcgcagtca ccaaaacttg tcctttcagt ttagccttaa ccggcgcatg acttcaagac     1740
taactcctct aaatcaatta ccagtggctg ctgccagtgg tgcttttgca tgtctttccg     1800
ggttggactc aagacgatag ttaccggata aggcgcagcg gtcggactga acgggggtt     1860 cgtgcataca gtccagcttg gagcgaactg cctacccgga actgagtgtc aggcgtggaa     1920
tgagacaaac gcggccataa cagcggaatg acaccggtaa accgaaaggc aggaacagga     1980
gagcgcacga gggagccgcc aggggaaacg cctggtatct ttatagtcct gtcgggtttc     2040
gccaccactg atttgagcgt cagatttcgt gatgcttgtc agggggcgg agcctatgga     2100 aaaacggctt tgccgcggcc ctctcacttc cct                                 2133
```

<210> SEQ ID NO 11
<211> LENGTH: 6499
<212> TYPE: DNA
<213> ORGANISM: Escherichia coli
<220> FEATURE:
<221> NAME/KEY: misc_feature
<222> LOCATION: (1545)..(1545)
<223> OTHER INFORMATION: n is a, c, g, or t
<220> FEATURE:
<221> NAME/KEY: Unsure
<222> LOCATION: (1546)..(1546)
<223> OTHER INFORMATION: pCA2 plasmid. Source of cat, sacB cassette.

<400> SEQUENCE: 11

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
```

```
tacgccagct ggcgaaaggg ggatgtgctg caaggcgatt aagttgggta acgccagggt    360
tttcccagtc acgacgttgt aaaacgacgg ccagtgccaa gcttgcatgc ctgcaggtcg    420
actctagagg atccccgggt accgagctcg aattcccgcg cccgatgaat tgatccgaag    480
ttcctattct ctagaaagta taggaacttc gaattgtcga caagctagca tgtgacggaa    540
gatcacttcg cagaataaat aaatcctggt gtccctgttg ataccgggaa gccctgggcc    600
aacttttggc gaaaatgaga cgttgatcgg cacgtaagag gttccaactt tcaccataat    660
gaaataagat cactaccggg cgtattttt gagttatcga ttttcagg agctaaggaa       720 gctaaaatgg agaaaaaaat cactggatat accaccgttg atatatccca atggcatcgt    780
aaagaacatt ttgaggcatt tcagtcagtt gctcaatgta cctataacca gaccgttcag    840
ctggatatta cggcctttt aaagaccgta agaaaaata agcacaagtt ttatccggcc      900
tttattcaca ttcttgcccg cctgatgaat gctcatccgg aattccgtat ggcaatgaaa    960
gacggtgagc tggtgatatg ggatagtgtt caccttgtt acaccgtttt ccatgagcaa    1020
actgaaacgt tttcatcgct ctggagtgaa taccacgacg atttccggca gtttctacac    1080
atatattcgc aagatgtggc gtgttacggt gaaaacctgg cctatttccc taaagggttt    1140
attgagaata tgtttttcgt ctcagccaat ccctgggtga gtttcaccag ttttgattta    1200
aacgtggcca atatggacaa cttcttcgcc cccgttttca ccatgggcaa atattatacg    1260
caaggcgaca aggtgctgat gccgctggcg attcaggttc atcatgccgt tgtgatggc     1320 ttccatgtcg gcagaatgct taatgaatta aacagtact gcgatgagtg cagggcggg     1380 gcgtaatttt tttaaggcag ttattggtgc ccttaaacgc ctggtgctac gcctgaataa    1440
gtgataataa gcggatgaat ggcagaaatt cgaaagcaaa ttcgacccgg tcgtcggttc    1500
agggcagggt cgttaaatag ccgcttatgt ctattgctgg tttantcggt acccggggat    1560
cgcggccgcg gaccggatcc catcacatat acctgccgtt cactattatt tagtgaaatg    1620
agatattatg atattttctg aattgtgatt aaaaaggcaa ctttatgccc atgcaacaga    1680
aactataaaa aatacagaga atgaaaagaa acagatagat tttttagttc tttaggcccg    1740
tagtctgcaa atccttttat gattttctat caaacaaaag aggaaaatag accagttgca    1800
atccaaacga gagtctaata gaatgaggtc gaaaagtaaa tcgcgcgggt ttgttactga    1860
taaagcaggc aagacctaaa atgtgtaaag ggcaaagtgt atactttggc gtcaccctt    1920 acatatttta ggtctttttt tattgtgcgt aactaacttg ccatcttcaa acaggagggc    1980
tggaagaagc agaccgctaa cacagtacat aaaaaggag acatgaacga tgaacatcaa    2040
aaagtttgca aaacaagcaa cagtattaac ctttactacc gcactgctgg caggaggcgc    2100
aactcaagcg tttgcgaaag aaacgaacca aaagccatat aaggaaacat acggcatttc    2160
ccatattaca cgccatgata tgctgcaaat ccctgaacag caaaaaaatg aaaatatca     2220 agttcctgaa ttcgattcgt ccacaattaa aaatatctct tctgcaaaag gcctggacgt    2280
ttgggacagc tggccattac aaaacgctga cggcactgtg caaactatca cggctaccac    2340
atcgtctttg cattagccgg agatcctaaa aatgcggatg acacatcgat ttacatgttc    2400
tatcaaaaag tcgcgaaac ttctattgac agctggaaa acgctggccg cgtctttaaa     2460
gacagcgaca aattcgatgc aaatgattct atcctaaaag accaaacaca agaatggtca    2520
ggttcagcca catttacatc tgacggaaaa atccgtttat tctacactga tttctccggt    2580
aaacattacg gcaaacaaac actgacaact gcacaagtta acgtatcagc atcagacagc    2640
```

```
tctttgaaca tcaacggtgt agaggattat aaatcaatct ttgacggtga cggaaaaacg    2700
tatcaaaatg tacagcagtt catcgatgaa ggcaactaca gctcaggcga caaccatacg    2760
ctgagagatc ctcactacgt agaagataaa ggccacaaat acttagtatt tgaagcaaac    2820
actggaactg aagatggcta ccaaggcgaa gaatctttat ttaacaaagc atactatgca    2880
aaagcacatc attcttccgt caagaaagtc aaaaacttct gcaaagcgat aaaaaacgca    2940
cggctgagtt agcaaacggc gctctcggta tgattgagct aaacgatgat tacacactga    3000
aaaaagtgat gaaaccgctg attgcatcta acacagtaac agatgaaatt gaacgcgcga    3060
acgtctttaa aatgaacggc aaatggtacc tgttcactga ctcccgcgga tcaaaaatga    3120
cgattgacgg cattacgtct aacgatattt acatgcttgg ttatgtttct aattcttttaa   3180 ctggcccata caagccgctg aacaaaactg gccttgtgtt aaaaatggat cttgatccta    3240
acgatgtaac ctttacttac tcacacttcg ctgtacctca agcgaaagga aacaatgtcg    3300
tgattacaag ctatatgaca aacagaggat tctacgcaga caaacaatca acgtttgcgc    3360
cgagcttcct gctgaacatc aaaggcaaga aaacatctgt tgtcaaagac agcatccttg    3420
aacaaggaca attaacagtt aacaaataaa acgcaaaag aaaatgccaa tatcctattg     3480
gcattttctt ttatttcttc catttaaatg gatgcatgcg ctagcggagt gtatactggc    3540
ttactatgtt ggcactgatg agggtgtcag tgaagtgctt catgtggcag agaaaaaag    3600 gctgcaccgg tgcgtcagca gaatatgtga tacaggatat attccgcttc ctcgctcact    3660
gactgctgag ctcatgagcg gagaacgaga tgacgttgga ggggcaaggt cgcgctgatt    3720 gctgggcaa cacgtgaaag gcgagatcac caaggtagtc ggcaaataat gtctaacaat     3780
tcgttcaagc cgacgccgct tcgcggcgcg gcttaactca agcgttagat gcactaagca    3840
cataattgct cacagccaaa ctatcaggtc aagtctgctt ttattatttt taagcgtgca    3900
taataagccc tacacaaatt gggagatata tcatgaaagg ctggcttttt cttgttatcg    3960
caatagttgg cgaagtaatc gcaacatccg cattaaaatc tagcgagggc tttactaagc    4020
tgatccggtg gatgaccttt tgaatgacct ttaatagatt atattactaa ttaattgggg   4080
accctagagg tccccttttt tattttaaaa attttttcac aaaacggttt acaagcataa    4140
agctcgatga attgatccga agttcctatt ctctagaaag tataggaact tcgaattgtc    4200
gacaagctcc ccggggagct tgatctggct tatcgaaatt aatacgactc actataggga    4260
gaccggaatt cgtaatcatg gtcatagctg tttcctgtgt gaaattgtta tccgctcaca    4320
attccacaca acatacgagc cggaagcata aagtgtaaag cctggggtgc ctaatagtga    4380
gctaactcac attaattgcg ttgcgctcac tgcccgcttt ccagtcggga aacctgtcgt    4440
gccagctgca ttaatgaatc ggccaacgcg cggggagagg cggtttgcgt attgggcgct    4500
cttccgcttc ctcgctcact gactcgctgc gctcggtcgt tcggctgcgg cgagcggtat    4560
cagctcactc aaaggcggta atacggttat ccacagaatc aggggataac gcaggaaaga    4620
acatgtgagc aaaaggccag caaaaggcca ggaaccgtaa aaaggccgcg ttgctggcgt    4680
ttttccatag gctccgcccc cctgacgagc atcacaaaaa tcgacgctca agtcagaggt    4740
ggcgaaaccc gacaggacta taaagatacc aggcgtttcc ccctggaagc tccctcgtgc    4800
gctctcctgt tccgaccctg ccgcttaccg gatacctgtc cgcctttctc ccttcggagc    4860
gtggcgcttt ctcaaagctc acgctgtagg tatctcagtt cggtgtaggt cgttcgctcc    4920
aagctgggct gtgtgcacga accccccgtt cagcccgacc gctgcgcctt atccggtaac    4980
tatcgtcttg agtccaaccc ggtaagacac gacttatcgc cactggcagc agccactggt    5040
```

```
aacaggatta gcagagcgag gtatgtaggc ggtgctacag agttcttgaa gtggtggcct    5100
aactacggct acactagaag aacagtattt ggtatctgcg ctctgctgaa gccagttacc    5160
ttcggaaaaa gagttggtag ctcttgatcc ggcaaacaaa ccaccgctgg tagcggtggt    5220 tttttgttt gcaagcagca gattacgcgc agaaaaaaag gatctcaaga agatcctttg    5280
atcttttcta cggggtctga cgctcagtgg aacgaaaact cacgttaagg gattttggtc    5340
atgagattat caaaaaggat cttcacctag atccttttaa attaaaaatg aagttttaaa    5400
tcaatctaaa gtatatatga gtaaacttgg tctgacagtt accaatgctt aatcagtgag    5460
gcacctatct cagcgatctg tctatttcgt tcatccatag ttgcctgact ccccgtcgtg    5520
tagataacta cgatacggga gggcttacca tctggcccca gtgctgcaat gataccgcga    5580
gacccacgct caccgctcc agattatca gcaataaacc agccagccgg aagggccgag    5640
cgcagaagtg gtcctgcaac tttatccgcc tccatccagt ctattaattg ttgccgggaa    5700
gctagagtaa gtagttcgcc agttaatagt ttgcgcaacg ttgttgccat tgctacaggc    5760
atcgtggtgt cacgctcgtc gtttggtatg gcttcattca gctccggttc ccaacgatca    5820
aggcgagtta catgatcccc catgttgtgc aaaaaagcgg ttagctcctt cggtcctccg    5880
atcgttgtca gaagtaagtt ggccgcagtg ttatcactca tggttatggc agcactgcat    5940
aattctctta ctgtcatgcc atccgtaaga tgcttttctg tgactggtga gtactcaacc    6000
aagtcattct gagaatagtg tatgcggcga ccgagttgct cttgcccggc gtcaatacgg    6060
gataataccg cgccacatag cagaacttta aaagtgctca tcattggaaa acgttcttcg    6120
gggcgaaaac tctcaaggat cttaccgctg ttgagatcca gttcgatgta acccactcgt    6180
gcacccaact gatcttcagc atcttttact ttcaccagcg tttctgggtg agcaaaaaca    6240
ggaaggcaaa atgccgcaaa aaagggaata agggcgacac ggaaatgttg aatactcata    6300
ctcttccttt ttcaatatta ttgaagcatt tatcagggtt attgtctcat gagcggatac    6360
atatttgaat gtatttagaa aaataaacaa ataggggttc cgcgcacatt tccccgaaaa    6420
gtgccacctg acgtctaaga aaccattatt atgatgacat taacctataa aaataggcgt    6480
atcacgaggc cctttcgtc                                                 6499
```

FERMENTATION OF GLYCEROL TO ORGANIC ACIDS

The application is the U.S. national stage application of International Patent Application No. PCT/US2011/045001 filed on Jul. 22, 2011.

The Sequence Listing for this application is labeled "MC2014-01US_ST25.txt" which was created on Jan. 20, 2014 and is 14 KB in size. This sequence listing is same as the one submitted with the PCT Application filed on Jul. 22, 2011 except this sequence listing has been amended to include PCT Application number and the date on which the PCT Application was filed. The content of the sequence listing is incorporated herein by reference in its entirety.

FIELD OF THE INVENTION

This patent application relates to production of organic acids from glycerol by fermentation using genetically engineered microorganisms.

BACKGROUND OF THE INVENTION

Large scale processes have been developed and are being used commercially to convert glycerol esters of fatty acids (also known as glycerides, mono-glycerides, di-glycerides, and tri-glycerides) to glycerol esters of methanol, ethanol, or other alcohols. The resulting fatty acid esters (also known as FAME for fatty acid methyl ester or FAEE for fatty acid ethyl ester) are commonly known as "biodiesel", because they can be used by themselves or in blends with conventional hydrocarbons as fuel for diesel engines. The raw materials for the synthesis of biodiesel can include vegetable oil, animal fats, and discarded cooking oil. A major volume byproduct of the biodiesel process is glycerol (also known as glycerin or glycerine). For each kilogram of biodiesel produced, about 0.1 kilogram of glycerol byproduct is produced.

When the catalyst for biodiesel synthesis is sodium hydroxide or potassium hydroxide, the glycerol byproduct is typically about 80% to 90% glycerol by weight, with the remainder of the byproduct being mostly water, methanol or ethanol (depending on which alcohol was used for the transesterification), various salts, and low levels of other organic compounds. The raw glycerol byproduct is alkaline and viscous, so it is usually neutralized down to a pH of about 4 or 5 with sulfuric acid, hydrochloric acid, or other acid, which reduces the viscosity and leaves the presence of the resulting salts, such as sodium chloride, sodium sulfate, potassium chloride, potassium sulfate, etc., with the exact composition obviously depending on the compounds used in the process. Much or all of the alcohol can typically be removed and recovered from the crude glycerol by distillation. The sodium or potassium hydroxide catalyst used in this type of process is called a homogeneous catalyst.

Another process for producing biodiesel relies on a "heterogeneous catalyst". An example of this is called Esterfip-H, commercialized by the French company Axens. The exact nature of this catalyst is proprietary, but it is reported to be a spinel mixed oxide of two non-noble metals, and it is reported to give a much cleaner glycerol byproduct than that from a homogeneous catalyst. The glycerol byproduct from a heterogeneous catalyst is reported to be 98% pure and free of salts (Ondrey, 2004).

With the growth of the biodiesel business there has of necessity been a parallel growth in the volume of glycerol byproduct. Some of the crude glycerol byproduct from biodiesel industry is purified by distillation and used in various industries that have classically used glycerol as a feedstock, and the rest of the glycerol from the biodiesel industry is considered to be a burdensome waste product. As a result, the value of the crude glycerol has plummeted to $0.05/lb or less in recent years (De Guzman, 2010). As such, glycerol has become a potentially inexpensive alternative to sugars and other carbohydrates such as glucose, fructose, sucrose, maltose, starch, and inulin, as a fermentation feedstock for production of fuels and chemicals (Clomburg and Gonzalez, 2010; Yazdani and Gonzalez, 2007). As of this writing, glucose and sucrose cost about $0.15 to $0.25/lb, and therefore a fermentation process that can use glycerol instead of other sugars could result in a substantial economic advantage.

A number of microorganisms have been developed for the commercial production of useful chemicals via fermentation using renewable sugars. *Escherichia coli* (*E. coli*) strains capable of producing organic acids in significant quantities using a variety of sugars as the source of carbon are well known in the art. For example, the U.S. Patent Application Publication No. 2009/0148914 provides strains of *E. coli* as a biocatalyst for the production of chemically pure acetate and/or pyruvate. The U.S. Pat. No. 7,629,162 provides derivatives of *E. coli* KO11 strain constructed for the production of lactic acid. International Patent Application Nos. WO 2008/115958 and WO 2010/115067 published under the Patent Cooperation Treaty provide microorganism engineered to produce succinate and malate in a minimal salt medium containing glucose as a source carbon in pH-controlled batch fermentation. U.S. Pat. No. 7,241,594 and U.S. Pat. No. 7,470,530 and the International Patent Application Publication No. WO 2009/024294 provides rumen bacterium *Mannheimia succiniproducens* useful in the fermentative production of succinic acid using sugars as the source of carbon. U.S. Pat. Nos. 5,000,000, 5,028,539, and 5,424,202 provide *E. coli* strains for the production of ethanol. U.S. Pat. Nos. 5,482,846, 5,916,787, and 6,849,434 provide gram-positive microbes for ethanol production. U.S. Pat. No. 7,098,009 provides *Bacillus* strains for the production of L(+) lactic acid. U.S. Pat. Nos. 7,223,567, 7,244,610, 7,262,046, and 7,790,416 provide *E. coli* strains for the production of succinic acid.

Most of the microbial organisms currently used in the biotechnology industry for the production of fuels and chemicals have a dedicated metabolic pathway for glycerol utilization. However, none of these industrial microorganisms have ever been shown to have the capacity to use glycerol as a feedstock with production parameters that are attractive for commercial manufacturing. This inability of the industrial microorganism to utilize glycerol as a commercial feedstock in the manufacturing of useful chemicals is attributed to certain regulatory metabolic feedback control mechanisms that are operational within the microbial cells.

The uptake and metabolism of glycerol by microorganisms has been well studied, particularly in *Escherichia coli* (Lin, 1996; Gonzalez et al., 2008). As shown in FIG. 1, in *E. coli*, glycerol enters the cell by a facilitated diffusion protein encoded by the glpF gene. In the "classical" glycerol metabolic pathway, glycerol is phosphorylated by glycerol kinase, encoded by the glpK gene, to give glycerol-3-phosphate (G3P). The G3P is then reduced to dihydroxyacetone phosphate by either the G3P dehydrogenase encoded by glpD or the three-subunit G3P dehydrogenase encoded by glpABC. The GlpK-GlpD/GlpABC pathway is considered to be respiratory route as it requires electron acceptors and is believed to be operational under aerobic conditions or when an alternative electron acceptor is present, such as nitrate or fumarate.

Another pathway for glycerol metabolism within the microbial cell is referred to as the non-classical pathway and is thought to be operational under anaerobic conditions (Gonzalez et al., 2008). In this second pathway, glycerol transported into the cell is reduced to dihydroxyacetone by a glycerol dehydrogenase encoded by gldA. The dihydroxyacetone is then phosphorylated by a phosphoenolpyruvate-dependent dihydroxyacetone kinase encoded by dhaKLM. The dihydroxyacetone phosphate resulting from either of these pathways can enter into the glycolytic pathway through triose phosphate isomerase, encoded by tpi. Triose-phosphate isomerase converts dihydroxyacetone phosphate into glyceraldehyde-3-phosphate which can enter into the tricarboxylic acid pathway after conversion into glycerate-1,3-diphosphate which in turn is converted into phosphoenolpyruvate.

There are several reports that disclose microbial production of various compounds by fermentation from glycerol. In general, the chemicals produced via microbial fermentation from glycerol, including succinate, ethanol, 1,2-propanediol, hydrogen, and formate, are produced at titers that do not appear to be high enough to compete with other known commercial processes for producing those compounds (Gonzalez et al., 2008; Durnin et al., 2009; Yazdani and Gonzalez, 2008).

Blankenschein et al. (2010) described an engineered E. coli strain that is contains ΔadhE, Δpta, ΔpoxB, ΔldhA, Δppc, and a plasmid pZS-pyc that over-expresses pyruvate carboxylase from Lactococcus lactis. Preliminary experiments with GldA-DhaKLM expressed from a separate vector in the ΔadhE, Δpta, ΔpoxB, ΔldhA, Δppc, [pZS-pyc] stain showed no improvements in succinate production. There are certain disadvantages with this glycerol utilizing strain of E. coli. This strain, which was not given a specific name, produced only 14 g/l of succinate in 72 hours with a yield of 0.69 g/g glycerol. Moreover, the plasmid pZS-pyc requires chloramphenicol for maintenance and anhydrotetracycline for induction, both of which are undesirable for large scale fermentations.

Yazdani and Gonzalez (2008) describe two E. coli strains, SY03 and SY04, designed to produce ethanol plus hydrogen or formate, respectively. These two strains also require the plasmid pZSKLMGldA. This plasmid is designed to over express the E. coli dhaKLM operon and gldA, which presumably increases flux through the "non-classical" glycerol pathway. In the most favorable example given, SY04 containing pZSKLMGldA produced about 10 g/l ethanol and 9 g/l formate from about 22 g/l glycerol, in 100 hours. These fermentation parameters are not high enough for a competitive commercial process. Moreover, the pZSKLMGldA plasmid requires chloramphenicol for maintenance and anhydrotetracycline for induction, both of which are undesirable for large scale fermentations.

The International Patent Application Publication No. WO 2010/051324 discloses E. coli strains with the plasmids LA01 (pZSglpKglpD) and LA20 (pZSglpKglpD) overexpressing glpK and glpD genes to produce D-lactate and L-lactate, respectively.

Zhang et al. (2010) have described an engineered E. coli strain, XZ721, that contains a mutation in the promoter region of pck gene (called pck*), ΔptsI, and ΔpflB. In fermentors, strain XZ721 using glycerol as a source of carbon produced 12 g/l succinate in 6 days, with a yield of 0.80 mol/mol glycerol used, which is equivalent to 1.02 g/g glycerol used. Deletion of gldA or dhaM in the pck* background led to higher succinate titers (13.2 g/l and 12.7 g/l respectively), suggesting that the GldA-DhaKLM route might not be the preferred pathway for succinate production under the fermentation conditions used.

Scholten et al. have recently isolated a novel ruminant bacterium in the Pasteurellaceae family that was named DD 1 or *Basfia succiniciproducens*. The DD 1 bacterium produces succinate from glycerol anaerobically (US Patent Application 2011/0008851). However, *Basfia succiniciproducens* does not grow on a minimal medium without added nutrients, and the maximum reported titer was 35 g/l succinate from glycerol as the sole carbon source. If maltose was added to the medium, the titer was improved to 58 g/l, but a significant amount of glycerol remained unused.

Trinh and Srienc (2009) reported improving the production of ethanol from glycerol by using elementary mode analysis to design an optimal *E. coli* strain. The optimal strain, TCS099 was then constructed, with a genotype of Δzwf, Δndh, ΔsfcA, ΔmaeB, ΔldhA, ΔfrdA, ΔpoxB, Δpta, and Δmdh. After metabolic evolution, TCS099 containing a plasmid, pLOI297, which expressed *Zymomonas mobilis* ethanol production genes, was able to produce ethanol from glycerol at up to 97% of theoretical yield and titer of about 17 g/l from 40 g/l glycerol. However, this process would again not be economically competitive with other current processes. The authors pointed out that mutations in glycerol kinase can increase the specific growth rate of strains on glycerol, as was known in 1970 (Zwaig et al., 1970), and they suggested that their evolved strain might have generated an increase in flux through glycerol kinase through a mutation, but they did not sequence or characterize the glycerol kinase gene in their evolved strain, and they did not suggest that deliberate introduction of a mutated glycerol kinase would increase rate of ethanol production or lead to a higher ethanol titer with glycerol as the source of carbon.

Since the industrial scale microbial production of biofuels and organic chemicals is carried out under anaerobic fermentative conditions, it is logical to activate the anaerobic glycerol utilization pathway inside the microbial cell in order to make the microorganisms to utilize glycerol as the feedstock. But as described above, the genetic manipulation of the anaerobic glycerol utilization pathway has not produced expected improvements in the production of desired chemicals using glycerol as the sole source of carbon. There has been disclosures in the prior art of feedback resistant alleles of glpK and of regulation of expression of glycerol utilization genes in the aerobic glycerol utilization pathway by the repressor protein coded by glpR gene. However, no effort has ever been made to improve the production of commercially useful chemicals from glycerol by replacing the wild type glpK allele in a production strain with a feedback resistant glpK allele or by deleting the repressor of glycerol utilization, such as the *E. coli* glpR gene, or a combination of the two approaches. The present inventors have surprisingly found out that by means of engineering the GlpK-GlpD/GlpABC route for glycerol utilization followed by a process of metabolic evolution in the microbial cells selected for the production of succinic acid, it is possible to confer the ability to utilize glycerol as the source of carbon, while retaining the original production capacity for succinic acid. Although the present invention is explained in detail with the construction of an *E. coli* strain suitable for the commercial production of succinic acid using glycerol as the source of carbon, the general theme and the spirit of the present invention can be applied in the construction of the microbial strains for the production of a number of other commercially useful chemicals using glycerol as the source of carbon in a microbial fermentation process.

SUMMARY OF THE INVENTION

The present invention provides microorganisms and the processes for the production of one or more chemicals of commercial interest through biological fermentation using glycerol as a carbon source. Using glycerol as a source of carbon and the microorganisms and the processes of the present invention, one can manufacture a variety of chemicals of commercial interest including but not limited to succinic acid, lactic acid, malic acid, fumaric acid, 1,2-propanediol, 1,3-propanediol, 1,4-butanediol, ethanol and acetic acid.

In a preferred embodiment, the glycerol suitable for the present invention is derived from the biodiesel industry. In a most preferred embodiment, the present invention uses glycerol derived from the biodiesel industry from which contaminating compounds have been removed. In one aspect, the glycerol derived from biodiesel industry is free of contaminating compounds such as methanol and ethanol. In another aspect of the present invention, the glycerol derived from the biodiesel industry is free of contaminating ions including but not limited to sodium, potassium, calcium, magnesium, ammonium, chloride, sulfate, phosphate, and mixtures thereof.

In another embodiment, the present invention provides a microorganism suitable for the manufacture of one or more chemicals of commercial interest using glycerol as a source of carbon wherein said microorganism comprises a deregulated glycerol utilization pathway and the glycerol utilization pathway comprises a facilitated diffuser, a glycerol kinase, and glycerol-3-phosphate dehydrogenase.

In one aspect of the present invention, deregulation of the glycerol utilization pathway involves a mutation in a glpR gene or other regulatory gene that results in a substantial decrease in the activity of a repressor that negatively regulates expression of glycerol utilization genes.

In another aspect of the present invention, deregulation of glycerol utilization pathway involves replacing the promoter region of the glpK, glpF, glpD and glpABC genes with the DNA sequence that would act as a constitutive promoter In yet another embodiment, the present invention provides microorganisms for the production of one or more chemicals of commercial interest using glycerol as a source of carbon, wherein the microorganisms have a mutation in a glpK gene or other gene encoding a glycerol kinase which confers resistance to feedback inhibition.

In one aspect, the present invention provides a microorganism comprising a mutation in a glpK gene that causes the specific activity of glycerol kinase to be substantially resistant to inhibition by fructose-1,6-bisphospate.

In another aspect, the present invention provides a microorganism comprising a mutation in a glpK gene that causes the specific activity of glycerol kinase to be substantially resistant to inhibition by a non-phosphorylated Enzyme IIA$^{Glc}$ of a phosphotransferase system.

In yet another aspect, the present invention provides microorganisms comprising two or more mutations, one of which causes the activity of a repressor that negatively regulates expression of glycerol utilization genes to be substantially decreased, and another of which causes the specific activity of a glycerol kinase to be substantially resistant to inhibition by fructose-1,6-bisphosphate and/or by a non-phosphorylated Enzyme IIA$^{Glc}$ of the phosphotransferase system.

In another embodiment, the present invention provides a method for producing one or more chemicals of commercial interest using glycerol as a source of carbon, wherein the method comprises microaeration.

In one aspect, the present invention provides a method for producing chemicals of commercial interest using glycerol as a source of carbon, wherein the fermentation broth is provided with less than 0.15 liters of oxygen per liter of broth per minute.

In another aspect, the present invention provides a method for producing chemicals of commercial interest using glycerol as a source of carbon wherein the fermentation broth is provided with at least 20 mg of oxygen per liter of broth per hour.

DETAILED DESCRIPTION OF THE PREFERRED EMBODIMENTS

Figure 1:
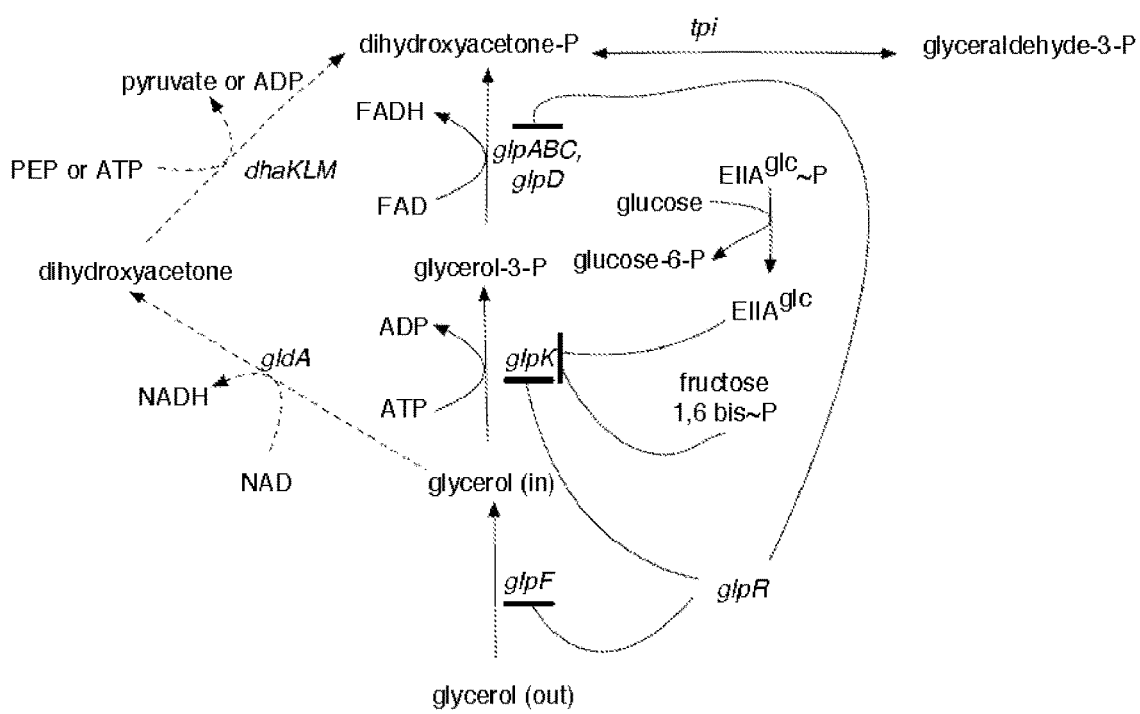
FIG. 1 Metabolic pathway for glycerol utilization in microorganisms. Glycerol import from the external environment into the microbial cell is mediated by a facilitated diffusion protein coded by glpF gene. Once within the cell, the glycerol can be metabolized to dihydroxyacetone phosphate. One of the two pathways considered to be operational under anaerobic conditions involves the proteins coded by gldA and dhaKLM genes. This pathway is shown by broken lines in the illustration. The other pathway for glycerol metabolism within the microbial cell is generally considered to be active under aerobic conditions, or when an alternative electron acceptor such as nitrate or fumarate is present, and is referred to as the classical pathway for glycerol utilization. The classical pathway for glycerol utilization within the microbial cell is shown by continuous line in the illustration. The genes glpF, glpK, glpD and glpABC code for the proteins involved in the operation on the classical pathway. Not shown in the figure is the glpX gene, which is in an operon together with glpF and glpK (the glpFKX operon), and which encodes a fructose-1,6-bisphosphate phosphatase that contributes to gluconeogenesis when the cell is growing on glycerol. Also shown in the figure are the regulatory mechanisms controlling the proteins involved in the operation of the classical pathway for glycerol metabolism. The repressor protein coded by the glpR gene controls the transcription of the glpFKXX, glpABC and glpD genes/operons. The glycerol kinase coded by glpK gene is also subjected to feedback inhibition by fructose-1,6-bisphosphate (FBP) and by the unphosphorylated form of EIIA$^{glc}$, a component of the phosphotransferase sugar transport system. Dihydroxyacetone phosphate, the end product of glycerol metabolism is converted into glyceraldehyde-3-phosphate through the action of triose phosphate isomerase coded by the tpi gene. Glyceraldehyde-3-phosphate acts as the starting point for the production of biofuels and organic acids within the microbial cells.

A number of industrially useful chemicals of commercial interest can be manufactured using the present invention. Most of these chemicals of commercial interest are intermediates in microbial metabolism. In the present invention, the microbial genome and growth conditions are appropriately manipulated to produce one or more of these microbial intermediates in significant quantities in a commercially successful way. Examples of such chemicals include, but are not limited to, ethanol, butanols, lactate, succinate, fumarate, malate, threonine, methionine and lysine. Since organic acids can exist both as free acids and as salts (for example, but not limited to, salts of sodium, potassium, magnesium, calcium, ammonium, etc.). Chemical names such as succinic acid, fumaric acid, malic acid, aspartic acid, threonine, methionine, and lysine shall be meant to include both the free acid and any salt thereof. Likewise, any salt, such as succinate, fumarate, malate, aspartate, etc., shall be meant to include the free acid as well.

The present invention combines the technique of specific genetic modifications with the process of metabolic evolution to obtain strains showing high yield, titer and volumetric productivity for succinic acid production under anaerobic or microaerobic growth conditions in a mineral salt medium with a glycerol as a carbon source.

For the purpose of the description of the present invention, the following definitions shall be used.

As used in the present invention, the term "titer" means the gram per liter or molar concentration of particular compound in the fermentation broth. Thus in the fermentation process for the production of succinic acid according to the present invention, a succinic acid titer of 100 mM would mean that the fermentation broth at the time of measurement contained 100 mMoles per liter or 11.8 grams per liter (g/l) of succinic acid in the fermentation broth.

As used in the present invention, the term "yield" refers to the moles of a particular compound produced per mole of the carbon source consumed during the fermentation process, or the grams of a particular compound produced per gram of carbon source consumed during the fermentation process. Thus in the fermentative process for the production of succinic acid using glycerol as a carbon source, the term yield refers to the number of grams of succinic acid produced per gram of glycerol consumed.

As used in the present invention, the term "volumetric productivity" refers to the amount of particular compound in grams produced per unit volume per unit time. Thus a volumetric productivity value of 0.9 g $L^{-1}h^{-1}$ for succinic acid would mean that 0.9 gram succinic acid is accumulated in one liter of fermentation broth during an hour of growth.

As used in the present invention, the term "gene" includes the open reading frame or frames of a DNA sequence as well as the upstream and downstream regulatory sequences. The upstream regulatory region is also referred as the promoter region of the gene. The downstream regulatory region is also referred as the terminator sequence region.

The phrase "functionally similar" means broadly any wild type or mutated DNA sequence, gene, enzyme, protein, from any organism, that has a biological function that is equivalent or similar to any wild type or mutated DNA sequence, gene, enzyme, protein that is found in the same or a different organism by the methods disclosed herein. Functional similarity need not require sequence homology. An allele is one of two or more forms of DNA sequence of a particular gene. Through mutations, each gene can have different alleles. A gene without any mutation is referred as a wild type allele when compared to a corresponding gene that has a mutation.

A homolog is a gene related to a second gene by descent from a common ancestral DNA sequence. The term, homolog, may apply to the relationship between genes separated by the event of speciation or to the relationship between genes separated by the event of genetic duplication. Orthologs are genes in different species that evolved from a common ancestral gene by speciation. Normally, orthologs retain the same function in the course of evolution. Identification of orthologs is critical for reliable prediction of gene function in newly sequenced genomes. Speciation is the origin of a new species capable of making a living in a new way from the species from which it arose. As part of this process it has also acquired some barrier to genetic exchange with the parent species. Paralogs are genes related by duplication within a genome. Orthologs retain the same function in the course of evolution, whereas paralogs evolve new function, even if these are related to the original one.

A gene or protein with "altered activity" is broadly defined as gene or protein that produces a measurable difference in a measurable property when compared to the relevant wild type gene or protein. The altered activity could manifest itself in a general way by increasing or decreasing the growth rate or efficiency of succinate production of the strain containing the altered gene or protein. Other measurable properties include, but are not limited to enzyme activity, substrate specificity of an enzyme, kinetic parameters of an enzyme such as affinity for a substrate or rate, stability of an enzyme, regulatory properties of an enzyme, gene expression level, regulation of gene expression under various conditions, sensitivity to one or more inhibitors, etc.

As used in the present invention, the term mutation refers to genetic modifications done to the gene including the open reading frame, upstream regulatory region and downstream regulatory region. A gene mutation can result either in an up regulation or a down regulation or complete inhibition of the transcription of the open reading frame of the gene or a change in the activity of the protein encoded by the mutated gene. The gene mutations can be achieved either by deleting the entire coding region of the gene or a portion of the coding nucleotide sequence or by introducing a frame shift mutation, a missense mutation, and insertion, or by introducing a stop codon or combinations thereof. Mutations may occur in the structural genes coding for the proteins directly involved in the biological functions such as enzyme reactions or transport of the organic molecules across the cell membrane. Alternately, mutations may occur in the regulatory genes coding for the proteins which control the expression of the genes coding for the proteins directly involved in the biological functions. The proteins which control the expression of the other genes are referred as regulatory proteins and the genes coding for these regulatory proteins are referred as regulatory genes.

"Mutation" shall also include any change in a DNA sequence relative to that of the relevant wild type organism. For example, a mutation found in strain KJ122 is any change in a DNA sequence that can be found when the DNA sequence of the mutated region is compared to that of the parent wild type strain, *E. coli* C, also known as ATCC 8739. A mutation can be an insertion of additional DNA of any number of base pairs or a deletion of DNA of any number of base pairs. A particular type of insertion mutation is a gene duplication. A gene can be duplicated by a spontaneous mutational event, in which the second copy of the gene can be located adjacent to the original copy, or a gene can be duplicated by genetic engineering, in which the second copy of the gene can be located at a site in the genome that is distant from the original copy. A mutation can be a change from one base type to another base type, for example a change from an adenine to a guanine base. In the vernacular of genetics, a mutation can be a missense (which changes the amino acid coded for by a codon), a nonsense (which changes a codon into stop codon), a frameshift (which is an insertion or deletion of a number of bases that is not a multiple of three and which changes the reading frame and alters the amino acid sequence that is encoded downstream from the mutation, and often introduces a stop codon downstream from the mutation), or an inversion (which results from a DNA sequence being switched in polarity but not deleted). The symbol "Δ" in front of the name of a gene indicates that the coding sequence for that gene has either fully or partially been eliminated and the gene is functionally inactive.

A "null mutation" is a mutation that confers a phenotype that is substantially identical to that of a deletion of an entire open reading frame of the relevant gene, or that removes all measurable activity of the relevant gene.

A "mutant" is a microorganism whose genome contains one or more mutations.

As used in this invention, the term "exogenous" is intended to mean that a molecule or an activity derived from outside of a cell is introduced into the host microbial organism. In the case an exogenous nucleic acid molecule introduced into the microbial cell, the introduced nucleic acid may exist as an independent plasmid or may get integrated into the host chromosomal DNA. The exogenous nucleic acid coding for a protein may be introduced into the microbial cell in an expressible form with its own regulatory sequences such as promoter and terminator sequences. Alternatively, the exogenous nucleic acid molecule may get integrated into the host chromosomal DNA and may be under the control of the host regulatory sequences. The term "endogenous" refers to the molecules and activity that are present within the host cell. When used in reference to a biosynthetic activity, the term "exogenous" refers to an activity that is introduced into the host reference organism. The source can be, for example, a homologous or heterologous encoding nucleic acid that expresses the referenced activity following introduction into the host microbial organism. If the nucleic acid coding for a protein is obtained from the same species of the microbial organism, it is referred to as homologous DNA. If the nucleic acid derived from a different microbial species, it is referred to as heterologous DNA. Irrespective of the nature of the DNA, whether it is homologous or heterologous, when introduced into a host cell, the DNA as well as the activity derived from that introduced DNA is referred to as exogenous. Therefore, exogenous expression of an encoding nucleic acid of the invention can utilize either or both heterologous and homologous encoding nucleic acid.

The present invention provides microorganisms that can use glycerol as a source of carbon in the manufacturing of commercially useful chemicals. Although the present invention is demonstrated using *Escherichia coli* bacterium, this invention can be applied to wide range of bacterial species including *Citrobactor freundii, Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flave-*

*lus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus licheniformis, Bacillus subtilis, Bacillus amyloliquifaciens, Bacillus coagulans, Escherichia freundii, Microbacterium ammoniaphilum, Serratia marcescens, Salmonella typhimurium, Salmonella schottmulleri, Klebsiella oxytoca, Klebsiella pneumonia* and *Xanthomonas citri*. The present invention is also useful in conferring the ability to use glycerol as the source of carbon in those yeast strains selected for the production of a commercially useful chemical, for example, but not limited to, a yeast selected from the following genera: *Saccharomyces, Kluyveromyces, Candida, Zygosaccharomyces, Torulopsis, Torulospora, Williopsis, Issatchenkia, Pichia, Schizosaccharomyces, Phaffia, Cryptoccus, Yarrowia, Saccharomycopsis*, etc., Glycerol used as a feedstock in the present invention can be derived from the biodiesel industry. It is preferable to remove the contaminants in the glycerol derived from biodiesel industry before its use in the fermentation process for the production of commercially useful chemicals. In a preferred embodiment, the glycerol is derived from a biodiesel industry where a heterogeneous catalyst is used leading to the production of glycerol with minimal contaminating components. Some of the contaminants such as ethanol and methanol can be removed through distillation. Dilution of the original glycerol stock solution is yet another approach to reduce the effect of contaminants.

The glycerol byproduct from biodiesel manufacturing is known to contain some minority contaminating compounds, such as water, methanol or ethanol, and salt ions, such as sodium, potassium, magnesium, calcium, ammonium, chloride, sulfate, and phosphate. If this "crude" glycerol is diluted about five-fold to ten-fold, then the contaminating compounds will be diluted to concentrations that should be tolerated by microorganism, including microorganisms of the instant invention. Nonetheless, it is preferable to at least partially remove the contaminating compounds prior to fermentation. Since the glycerol is a large volume byproduct, and might be derived from more than one biodiesel manufacturing facility, there might be some unpredictable variability between batches, so it is possible that levels of the contaminants in some batches or lots might be undesirable. In addition, the ionic contaminants might be less expensive to remove prior to fermentation compared to removal after fermentation. In the event that the desired product (for example an organic acid) is desired to be free of one or more of the contaminants, the contaminants must be removed either before or after fermentation. For example, if the organic acid produced is destined to be chemically modified (for example, hydrogenated) and/or polymerized into a plastic, then all forms of sulfur and phosphorus must be at least partially removed in order to protect catalysts from being poisoned. As another example, the methanol or ethanol might also act as chain terminators during polymerization, since they only have one reactive group.

Lower alcohols such as methanol and ethanol can be removed by distillation and/or reduced pressure. The ionic contaminants can be removed by ion exchange resins. Since the glycerol is uncharged at non-extreme pH's, the crude glycerol can be passed over a cation exchange resin that started in the hydrogen ($H^+$) form, followed by passage over an anion exchange resin that started in the hydroxide ($OH^-$) form, or vice versa. Alternatively, the crude glycerol can be passed over a mixed bed ion exchange resin that contains a mixture of the two types of resin. Using the two different resins in series is preferable to a mixed bed, since regeneration of the resins is then easier. The ion exchanges can be done with columns or batch wise. Glycerol should not be bound by either type of resin, while the ions should be retained by the resins.

Ions can also be removed from crude glycerol by other well known methods, such as electrodialysis, or by filtration through membranes, either charged or uncharged, that can discriminate between glycerol and the undesirable contaminants. Glycerol can also be purified by distillation or vacuum distillation.

The microbial organisms suitable for the production of commercially useful chemicals can be obtained a number of different ways. According to a preferred embodiment, a microbial cell obtained through a combined process of genetic engineering and metabolic evolution for the production of a particular commercially useful chemical using a carbon source other than glycerol such as glucose is used as a parental strain. For example, the KJ122 strain of *E. coli* described in detail (Jantama et al., 2008a; Jantama et al., 2008b; Zhang et al., 2009a; Zhang et al., 2009b) can be used as a parental strain to obtain a strain capable of using glycerol as a source of carbon in the commercial production of succinic acid. In the first stage of generating a strain useful in the production of succinic acid using glycerol as the source of carbon, the KJ122 strain is subjected to specific genetic manipulations to enhance the uptake and metabolism of glycerol. The genetic manipulations of the glycerol metabolic pathway can be followed by a process of metabolic evolution to obtain a bacterial strain with a commercially attractive yield, titer, and productivity for the production of succinic acid using glycerol as the source of carbon.

Based on our current understanding of the glycerol metabolic pathway inside a microbial cell, one can identify appropriate targets for genetic manipulation within the glycerol metabolic pathway. FIG. 1 provides an overview of our current understating about the glycerol metabolic pathway within a microbial cell.

Entry of glycerol from the culture medium into the microbial cell is mediated by a facilitated diffusion protein encoded by glpF gene. Once inside the cell, glycerol is metabolized by two different routes leading to the formation of dihydroxyacetone phosphate. In one pathway considered to be active under anaerobic conditions, glycerol is acted upon by glycerol dehydrogenase encoded by gldA gene. The oxidation of glycerol by glycerol dehydrogenase yields dihydroxyacetone accompanied by the formation of NADH. In the next stage, dihydroxyacetone is phosphorylated by phosphoenolpyruvate-dependent or an ATP-dependent dihydroxyacetone kinase encoded by dhaKLM. This phosphorylation reaction leads to the formation of dihydroxyacetone phosphate. This pathway for glycerol metabolism is referred to as the non-classical pathway for glycerol metabolism.

In another route for glycerol metabolism within the microbial cell considered to be operative under aerobic conditions, or anaerobic conditions where an alternative electron acceptor is present, such as nitrate or fumarate, glycerol is phosphorylated to produce glycerol-3-phosphate. In the next step, the glycerol-3-phosphate is oxidized by glycerol-3-phosphate dehydrogenase encoded by GlpD or GlpABC leading to the formation of dihydroxyacetone phosphate. This pathway for glycerol metabolism is referred to the as classical pathway for glycerol metabolism.

Dihydroxyacetone resulting from both the classical and non-classical pathway for glycerol metabolism is acted upon by triosephosphate isomerase leading to the formation of glyceraldehyde-3-phosphate. The glyceraldehyde-3-phosphate thus formed can pass through the rest of the glycolytic pathway and ultimately enter into the tricarboxylic acid cycle leading to the accumulation of one or other metabolic intermediate based on the nature of the genetic alterations that have occurred in the glycolytic, fermentative and tricarboxylic acid cycle pathways.

Beside the difference in the nature of the enzymes and the cofactors involved, the classical and non-classical pathways for glycerol metabolism differ from each other in the nature of regulations controlling the operation of these two glycerol metabolic pathways.

The classical glycerol pathway is regulated in two different ways. First, expression of glpF, glpK, glpD, and glpABC are all repressed by a protein encoded by glpR in the presence of the intermediate, G3P. Second, the GlpK enzyme is inhibited by fructose 1,6 bisphosphate, and by the non-phosphorylated form of the phosphotransferase system (PTS) component, Enzyme $IIA^{Glc}$ (also called $EIIA^{Glc}$ and formerly called Enzyme $III^{Glc}$ or $EIII^{Glc}$), which, in the case of E. coli, is encoded by the crr gene. A consequence of these regulatory mechanisms is that utilization of glycerol is strongly inhibited when glucose is present in the medium. When cells are grown in the presence of glucose, the concentration of both inhibitors of GlpK increases. For the purposes of this patent application, the inhibition of GlpK activity by either fructose 1,6 bisphosphate or $EIIA^{Glc}$ is referred to as feedback inhibition or a negative regulatory mechanism. The term "deregulated glycerol pathway" is defined as a pathway for glycerol utilization in which one or more negative regulatory mechanisms that operate on a glycerol utilization pathway have been decreased in function or entirely removed by genetic changes in the host organism. Such genetic changes include, but are not limited to, 1) a decrease or elimination on function of a repressor such as GlpR, 2) an alleviation of some, or all, inhibition of a glycerol kinase such as GlpK by a metabolic intermediate such as fructose-1,6-bisphosphate or by a protein such as a non-phosphorylated form of a phosphotransferase system (PTS) component, such as Enzyme $IIA^{Glc}$, 3) a decrease in glucose inhibition of glycerol utilization, for example by decreasing a cells ability to import or metabolize glucose and/or 4) replacement of a native promoter of a glycerol utilization gene or operon, such as glpD, glpFKX and/or glpABC with a stronger or more constitutive promoter which is not subject to the repression by GlpR protein encoded by the glpR gene. A number of constitutively active promoters are well known in the art and any one of them can be used in the instant invention to replace the native promoter of glpFKX, glpD, and glpABC genes/operons, which are under the control of GlpR protein in a wild type bacterial cell. The replacement of a native promoter of any gene with a constitutively active promoter can be accomplished using one or other genetic engineering techniques well known in the art of microbial genetic engineering, such as the two-step allele replacement method described in Example 6, in which the native promoter is replaced by insertion of a cat, sacB cassette, which is subsequently replaced by a constitutively active promoter sequence well known in the art.

There are several reports of mutant alleles of glpK that are resistant to feedback inhibition by G3P, or non-phosphorylated Enzyme $IIA^{Glc}$, or both (Bell, 1974; Pettigrew et al., 1996). Some of these alleles were originally isolated by Cronan and Bell (Cronan and Bell, 1974a; Cronan and Bell, 1974b) in strains named BB20-14 and BB26-36, which were obtained from G3P auxotrophs by selection for growth on glucose plus glycerol. These strains were presumed to contain feedback resistant glycerol kinases. The DNA sequence of the glpK genes from those strains has not heretofore been published. The Coli Genetic Stock Center (CGSC) at Yale University, New Haven, Conn., USA can provide these two strains, and the curators have named the alleles in these two strains glpK15(fbR) and glpK14(fbR), respectively. For simplicity, in this specification, we shall call these alleles $glpK^i15$ and $glpK^i14$, respectively, where the "i" superscript denotes insensitive to feedback inhibition.

Another feedback resistant allele of glpK, named $glpK^i22$, was first isolated by Zwaig and Lin in a strain named Lin 43 (Zwaig and Lin, 1966), and was later characterized and sequenced by Pettigrew et al. (1996). The mutant was identified by its ability to incorporate radioactive glycerol in the presence of glucose.

Another approach that has been followed in isolating feedback resistant alleles of glpK was to select for suppression of certain PTS mutations (Berman and Lin, 1971). This approach gave rise to strain Lin 225, which contained a glycerol kinase that was resistant to inhibition by fructose 1,6-bisphosphate, but the glpK gene from that strain was never characterized. The glpK allele in strain Lin 225 was named $glpK^i31$ by the Coli Genetic Stock Center at Yale University.

Whole genome-sequencing of E. coli to monitor the acquisition and fixation of mutations that conveyed a selective growth advantage during adaptation to glycerol-based growth medium has identified a series of mutations in the gene for glycerol kinase (Iberra et al., 2002; Herring et al., 2006; Honisch et al., 2004). Partially purified protein from cells expressing the mutant glpK gene showed reaction rates for glycerol kinase enzyme 51%-133% higher than wild-type, and some of those mutants showed reduced inhibition of glycerol kinase by fructose-1,6-bisphosphate (Herring et al., 2006).

For purposes of this invention, a feedback resistant glycerol kinase is defined as a glycerol kinase that has higher specific activity than the related wild type enzyme in the presence of fructose 1,6-bisphosphate, or in the presence of the non-phosphorylated form of the phosphotransferase system (PTS) component, Enzyme $IIA^{Glc}$ from the same organism, or in the presence of both inhibitors. The feedback resistant property can be referred to in discussing the glycerol kinase enzyme, the gene encoding the glycerol kinase, or an allele of glycerol kinase.

Thus, four methods for isolating feedback resistant glpK alleles are known in the art: (1) Selection for growth of G3P auxotrophs on glucose plus glycerol, (2) Uptake of radioactive glycerol in the presence of glucose, (3) Suppression of a PTS Enzyme I mutant, and (4) Selection for more rapid growth in minimal glycerol medium (Bell, 1974; Zwaig and Lin, 1966; Berman and Lin, 1971; Honisch et al., 2006). Any one of those four methods can be made use of in the present invention in isolating a feedback resistant glpK allele. Although the examples provided in the present invention are based on E. coli, similar approach can be followed in any bacterial species and in particular in any other bacterial species of the genera Klebsiella, Salmonella, Enterobacter, Serratia, and Citrobacter.

Any one of these feedback resistant alleles of glpK can be used to replace the wild type glpK gene in a bacterial strain already developed for the production of a particular commercially important chemical. The wild type glpK gene in the KJ122 strain of E. coli already developed for the commercial production of succinic acid can be replaced with a mutant glpK allele which is resistant to feedback inhibition. Alternatively, the replacement of wild type glpK gene with a mutant allele of glpK can be accomplished in a wild type E. coli and the resulting bacterial strain with the mutant allele of glpK can be used as the parental strain in developing a strain for the commercial production of succinic acid.

The replacement of the wild type allele of glpK with a mutant allele of glpK can be accomplished by using one or other genetic engineering techniques well known in the art of microbial genetic engineering. In general, the wild type glpK gene in the parental strain is initially replaced by inserting an antibiotic marker gene at that locus. In the second stage, the antibiotic marker gene is replaced by a mutant allele of glpK. The mutant allele of glpK can be transferred from the strain reported to have a mutant allele of glpK to the recipient strain using a bacteriophage mediated transduction process. Alternatively, polymerase chain reaction can be used to clone the mutant allele from a recipient strain into a plasmid vector or directly into a chromosome. Subsequently, the plasmid vector with the mutant glpK allele can be used to transform the recipient bacterial strain. In another aspect of the present invention, when the nature of the mutation in the glpK gene is known at the nucleotide level, in vitro mutagenesis with synthetic oligonucleotides can be used to generate a mutant glpK allele in a plasmid vector. The mutant glpK allele from the plasmid vector can be used to replace the wild type glpK allele through transformation followed by double recombination. Alternatively, the mutant glpK allele contained on a linear DNA fragment can be used to replace the wild type glpK allele through transformation followed by double recombination.

In another embodiment of the present invention, deregulation of the glycerol pathway is conferred by means of overcoming the repression of expression of glpF, glpK, and glpABC genes by the repressor protein GlpR encoded by glpR gene. The repressive effect of GlpR protein can be overcome by two different ways. In the first method, the glpR gene sequence is altered so that the GlpR protein is no longer effective in repressing the expression of glpF, glpK, and glpABC genes. In the preferred embodiment, the synthesis of GlpR protein itself is inhibited. The inhibition of GlpR protein synthesis can be achieved by means of insertional inactivation of the glpR gene sequence. For example, an antibiotic marker cartridge can be inserted in the glpR open reading from so that the GlpR protein is no longer produced. In the most preferred embodiment, the glpR open reading frame is precisely removed and there is no foreign nucleotide sequence remaining at this locus.

In order to make sure that the glycerol utilization pathway within the microbial cell is fully deregulated, it is preferable to have feedback resistant glpK allele in addition to completely eliminating a functional glpR gene. These two genetic modifications can be carried out in a wild type bacterial strain to produce a parental bacterial strain with a completely deregulated glycerol utilization pathway. Subsequently the parental bacterial strain with a completely deregulated glycerol utilization pathway can further be subjected to specific genetic modifications and metabolic evolution to obtain a bacterial strain with high yield and productivity for the production of a particular metabolic product such as succinic acid or lactic acid. In the preferred embodiment, the inactivation of glpR gene and the introduction of feedback resistant allele of glpK are carried out in a strain that has already been genetically engineered and metabolically evolved for the production a particular commercially useful chemical. For example, the inactivation of glpR gene and the introduction of feedback resistant allele of glpK gene can be carried out in the KJ122 strain of E. coli already developed for the production of succinic acid using glucose as the source of carbon.

In another embodiment, the GlpR mediated repression of glpF, glpK, and glpABC gene expression is overcome by replacing the native promoter regions of glpF, glpK, and glpABC genes which is susceptible to regulation by GlpR repressor protein with a constitutive promoter not susceptible to repression by GlpR protein. In a preferred embodiment, in the bacterial strain with a constitutive promoter not susceptible to repression by GlpR, the wild type allele for glpK gene is replaced with a feedback resistant glpK allele. These two genetic modifications leading to the deregulation of glycerol utilization pathway can be carried out in a wild type bacterial strain leading to the formation of a parental strain with deregulated glycerol utilization pathway. Such a parental strain with a deregulated glycerol utilization pathway can further be subjected to genetic manipulations and metabolic evolution to produce a bacterial strain capable of producing a commercially useful chemical using glycerol as the source of carbon. Alternatively, replacement of the native promoters for glpF, glpK and glpABC genes with a well-defined constitutively active promoter and replacement of the wild-type allele for glpK with a feedback resistant glpK allele can carried out in a bacterial strain which is already developed for the commercial production of a specific chemical.

The microorganisms of the present invention are grown in a fermentation medium with microaeration. The preferred supply rate for oxygen (in the form of air at 40 ml/min in a 3 L starting volume) in the instant invention is about 0.0026/min, based on the starting volume of medium in the fermentor, which is equivalent to about 228 mg/liter-hour of oxygen. This rate is substantially lower than the optimal rate suggested by the prior art of Trinh and Srienc (2009), which was stated to be 0.15/min, and substantially higher than the optimal rate suggested by the prior art of Gonzalez and Campbell (WO/2010/051324), which was reported to be between 1 and 20 mg/liter-hour.

The term "genetically engineered" or "genetic engineering" as used herein refers to the practice of altering the expression of one or more enzymes in the microorganisms through manipulating the genomic DNA or a plasmid of the microorganism. The genomic manipulations involve either altering, adding or removing specific DNA sequences from the genomic DNA. The genetic manipulations also involve the insertion of a foreign DNA sequence into the genomic DNA sequence of the microorganism. In the most preferred embodiments of the present invention, some of the genetic manipulations are accomplished by means of removing specific DNA sequences from the genomic DNA of the microorganisms without introducing any foreign DNA. Certain genetic manipulations necessary to inactivate the expression of a gene coding for a particular protein product requires an insertion of a foreign DNA sequence into the genome of the microorganism. In the most preferred embodiment of the present invention, the introduced exogenous DNA sequences are ultimately removed from the genomic DNA of the microorganism so that the microorganism at the end of the genetic engineering process would have no exogenous DNA in its original genomic DNA. Various techniques necessary for accomplishing the objectives of the preferred embodiment of the present invention including the process for metabolic evolution have been described in detail in Jantama et al (2008a, 2008b). U.S. Pat.

No. 7,629,162 and U.S. Patent Application Publication No. US 2009/0148914 and the International Patent Applications published under the Patent Cooperation Treaty with International Publication Numbers WO 2008/115958 and WO 2010/115067 also describe the genetic engineering techniques useful in practicing various embodiments of this present invention. These scientific publications as well as the patent documents cited are herein incorporated by reference for the purpose of providing the details for genetic engineering techniques useful for the present invention.

Example 1

Removal of Negative Regulation of Glycerol Uptake and Utilization in Strain KJ122

Figure 2:
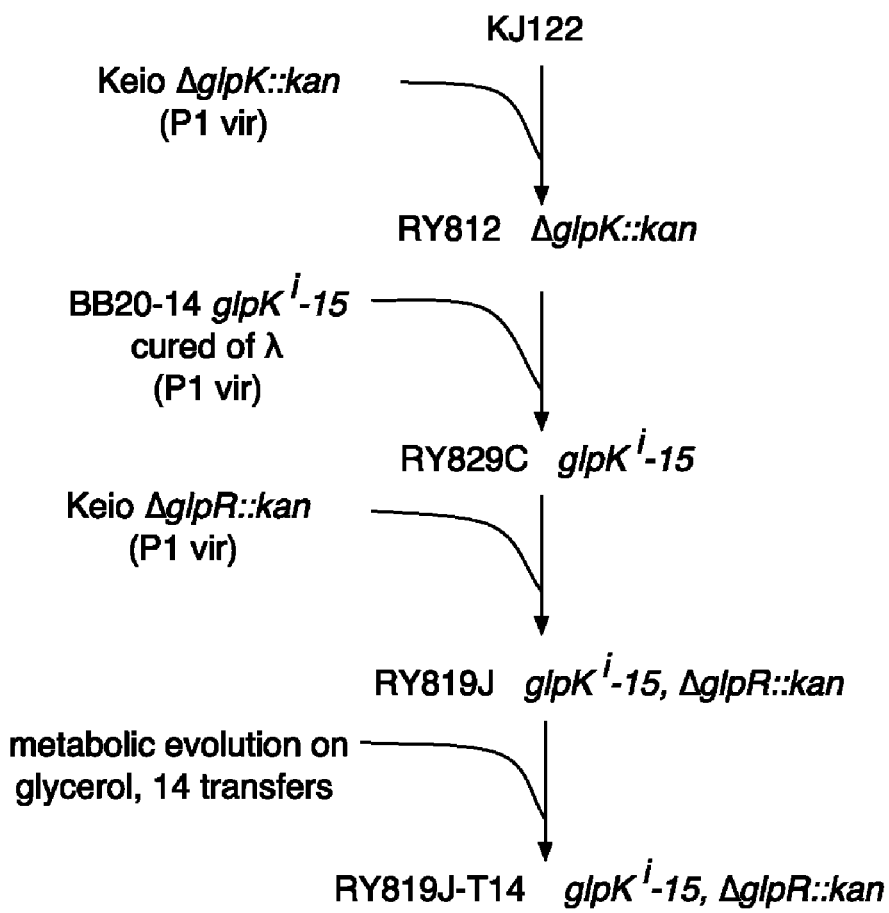
FIG. 2 Construction of glycerol utilizing RY819J-T14 strain from KJ122 E. coli strain. This illustration provides steps followed in the construction of an E. coli strain RY819J-T14. In the first stage of the construction of RY819J-T14, the wild type glpK gene in the KJ122 strain was replaced with a mutant form of glpK gene containing two point mutations leading to two amino acid substitutions. In the second stage, the glpR gene is inactivated with the insertion of a kanamycin resistant gene cartridge leading to the generation of the RY819J strain of E. coli. In the third stage, the RY819J strain of E. coli is subjected to metabolic evolution to obtain the RY819J-T14 strain of E. coli. Metabolic evolution of RY819J to obtain RY819J-T14 involved fourteen transfers as described in the specification.

Three different minimal media can be used for plate selections of bacterial strains, for succinate production in test tubes, or for succinate production in pH controlled fermentors. The minimal media are listed in Table 1. Rich broth or plates were Luria Broth, also known as "LB" (10 g/l tryptone, 5 g/l yeast extract, 5 g/l sodium chloride). The following strains were obtained from the Coli Genetic Stock Center (CGSC), Yale University, New Haven, Conn.: JW 3386-1 (ΔglpR::kan) and JW 3897-1 (ΔglpK::kan). Using generalized phage transduction with P1vir, the ΔglpK::kan allele from JW 3897-1 was installed in KJ122, selecting for kanamycin resistance using 50 mg/l kanamycin sulfate in LB plus 25 mM sodium citrate, and confirming correct installation of ΔglpK::kan by lack of growth on minimal plates with glycerol as the sole carbon source (FIG. 2). The resulting strain was named RY812. In parallel, the wild type lambda prophage residing in strain BB20-14 (obtained from John Cronan, University of Illinois, Champagne-Urbana, Ill.) was cured by P1vir transduction from strain TAP106 (also known as ATCC 47075) as the donor, which contains a defective lambda prophage that includes N::kan for selection, to give strain RY808, by selection for resistance to kanamycin as described above. In a second step, the glpK region from RY808, which contains the glpK$^i$15 allele, was transduced into RY812, selecting for growth on minimal SS glycerol plates (see Table 1), and confirming for loss of kanamycin resistance, to give strain RY829C. In a third step, the ΔglpR::kan allele of JW 3386-1 was transduced into RY829C, selecting for kanamycin resistance as described above, to give strain RY819J, which was an isolate that was shown to retain the nearby pck* allele (Zhang et al 2009a; Zhang et al., 2009b).

Example 2

Production of Succinate from Glycerol in Test Tubes

Strains KJ122 and RY819J were grown overnight aerobically in Luria Broth and then inoculated to give 0.05 $OD_{600}$ in 12.5 ml of NBS medium containing 20 g/l glycerol in 15 ml polypropylene test tubes with screw caps. The tubes were capped tightly and rolled on a New Brunswick Scientific roller drum at 37° C. at about 60 rpm for 48 hours. Culture samples were prepared by removing cells by centrifugation through Costar spin filters, diluted as necessary in 0.008M sulfuric acid, and analyzed by high pressure liquid chromatography (HPLC) using an Agilent Model 1200 apparatus installed with a BioRad Aminex HPX-87H column. The column was run at 50° C., with 0.008 M sulfuric acid as the solvent, and the detection was by both refractive index and absorption at 210 nm. Samples were analyzed for concentration of succinic acid, glycerol, glucose, acetate, and other byproducts. Concentrations of each chemical were calculated using standard curves derived from pure commercial compounds. KJ122 produced 0.06 g/l succinate, while RY819J produced 0.61 g/l succinate, a clear improvement over the starting strain.

Example 3

Metabolic Evolution of RY819J

Strain RY819J was grown overnight aerobically in NBS medium containing 10 g/l glucose and 10 g/l glycerol, and then inoculated into a 500 ml working volume covered fermentor containing 300 ml of AM1 medium (see Table 1) containing 50 g/l glycerol and 50 g/l glucose, to give a starting $OD_{600}$ of 0.2. The fermentor was stirred with a magnetic stirrer at 150 rpm, but no deliberate aeration was supplied. As such, the fermentor was not strictly anaerobic, since some air is admitted during sampling and from base addition. The pH was controlled at 6.5 by addition of 3M potassium carbonate, and the temperature was maintained at 40° C. Succinate was produced for about 48 hours, and glycerol and glucose were consumed in parallel, but after 48 hours, a portion of the glycerol remained. The final cell density was about 3.0 $OD_{600}$. A sample from the first fermentor was used to inoculate a second fermentor to a starting $OD_{600}$ of 0.2, using the same medium, and growth and succinate production resumed. This re-inoculation procedure shall be called a "transfer" in this specification. After succinate production ceased, a second transfer of inoculum to a third fermentor was done as above, followed by several more transfers. During the first few transfers, glucose was present in the medium to stimulate growth. In general, growth was slow in the first several transfers unless some glucose or potassium nitrate was present, so to obtain sufficient growth for subsequent transfers, some glucose or nitrate was added to the fermentors at various times to boost growth. The first four transfers started with 50 g/l glucose plus 50 g/l glycerol. Transfers 5 to 9 started with only 50 g/l glycerol and no glucose, but in order to obtain sufficient growth for the next transfer, 10 g/l glucose was added during the fermentation. Transfer 10 was supplemented first with 1 g/l potassium nitrate, and later with 10 g/l glucose. A summary of the additives and the times of the additions to the fermentors is given in Table 2. Starting with the 11$^{th}$ transfer, no glucose or nitrate was added to the medium; the sole carbon source was 50 g/l glycerol. Nonetheless, the growth eventually was sufficient to make a transfer. Samples were analyzed at various times by HPLC as described above. At transfer 11, after 384 hours, all of the glycerol had been consumed and the succinate titer was 425 mM, which was calculated after dilution with base to give a yield of 1.08 grams succinate per gram of glycerol consumed. Three more transfers were performed, but no further significant improvement in the performance of the strain in terms of succinic acid production was found. A single colony was isolated from the 14$^{th}$ transfer, and the isolate was named RY819J-T14 (FIG. 2).

Example 4

DNA Sequencing of Various glpK Allele

The wild type DNA sequences of the glpFKX operons of E. coli C (ATCC 8739) and E. coli K-12, from which many of the strains used herein were derived, can be found in the GenBank database at the National Institutes of Health, USA, accession numbers NC_010468 and NC_000913, respectively.

The glpK gene, surrounded by about half of the glpF gene and half of the glpX gene, was amplified by polymerase chain reaction (PCR) using genomic DNA from the following E. coli strains: BB20-14, BB26-36, Lin 225 and Lin 298. The latter three strains were all obtained from the Coli Genetic Stock Center (CGSC), Yale University, New Haven, Conn. According to the CGSC, these four strains namely BB20-14, BB26-30, Lin 225 and Lin 298 contain, among other mutations, glpK$^i$15, glpK$^i$14, glpK$^i$31, and glpK$^i$22, respectively. Of these, only glpK$^i$22 had been sequenced, revealing a G304S amino acid change (Pettigrew et al, 1996; Honisch et al, 2004). However, this sequence was derived from strain Lin 43, which was not available from CGSC. Therefore the instant inventors used Lin 298, which was available and is reported to be derived from Lin 43. The PCR primers used for the amplification were BY19 (SEQ ID no. 1) and BY44 (SEQ ID No. 2). DNA sequences of PCR and sequencing primers are given in Table 3. The reagents for PCR were the Phusion Master Mix from New England BioLabs, which was used as recommended by the supplier. The resulting blunt-ended DNA fragments from BB20-14, BB26-30, Lin 225 and Lin 298 were gel purified and cloned into the Eco RV site of pRY521 (SEQ ID No. 10), to give plasmids pMH4-20, pMH4-26, pMH4-225, and pMH4-298, respectively.

The glpK gene and flanking sequences from each of these plasmids was sequenced by the Sanger chain termination method using sequencing primers BY15 (SEQ ID No. 3), BY16 (SEQ ID No. 4), BY19 (SEQ ID No. 1), BY30 (SEQ ID No. 6), and BY44 (SEQ ID No. 2). Three of the four plasmids contained mutations in the glpK coding region. All DNA sequence coordinates given in this specification count the first base of the open reading frame as 1 and all amino acid coordinates count the start codon as 1. For the three letter amino acid codes, see the 2007-2008 New England BioLabs Catalog, p. 361. pMH4-20 had two point mutations in glpK (G163A; Ala55Thr and G470A; Arg157His) and, unexpectedly, a single point mutation in glpF (C821T; Pro274Leu).

pMH4-26 had a single point mutation in glpK (C164T; Ala55Val) and, unexpectedly, a single point mutation in glpF (G724A; Val242Ile). pMH4-225 had a single point mutation in glpK (C176A; Ser59Tyr) but no mutation in glpF. pMH4-298 had no mutation in the region sequenced. This latter result contradicts the published literature, which implies that strain Lin 298 should have the same glpK mutation as Lin 43 (see above). It appears that the isolate of Lin 298 that we used had somehow lost the glpK$^i$22 allele, or that our isolate was not in fact strain Lin 298, or that Lin 298 was not in fact derived from Lin 43.

The most likely interpretation of the above results is that the point missense mutations in the glpK genes accounts for the demonstrated or inferred feedback resistance of the encoded GlpK enzymes. Since the glpK$^i$15 allele contained two separated mutations, it is possible that either mutation by itself could confer a feedback resistant phenotype, but in any case, the inventors could conclude that the combination of the two mutations was sufficient for the feedback resistant phenotype of glycerol kinase in BB20-14.

In addition to the above plasmids, two similar plasmids were constructed from the glpK regions of KJ122 and RY819J, to give pMH4-KJ and pMH4-RY819 respectively. The DNA sequences of the cloned inserts were as expected. pMH4-KJ contained wild type glpK and glpF sequences, while pMH4-RY819 contained a sequence that was identical to that of pMH4-20, including the two point mutations in glpK and the single point mutation in glpF.

Example 5

Removal of the Kanamycin Resistance Gene from RY819J-T14

Strain RY819J-T14 contains the ΔglpR::kan allele transduced from strain JW 3386-1, which is a member of the "Keio Collection" (Baba et al., 2006). As such, the kanamycin resistance gene, kan, can be removed to leave a short DNA "scar" by passing a helper plasmid, pCP20, through the strain (Datsenko and Wanner, 2000). This process was performed on RY819J-T14 to give the kanamycin sensitive derivative, strain MH23.

Example 6

Correction of the Mutation Found in the glpF Gene of RY819J and Descendents

Figure 3:
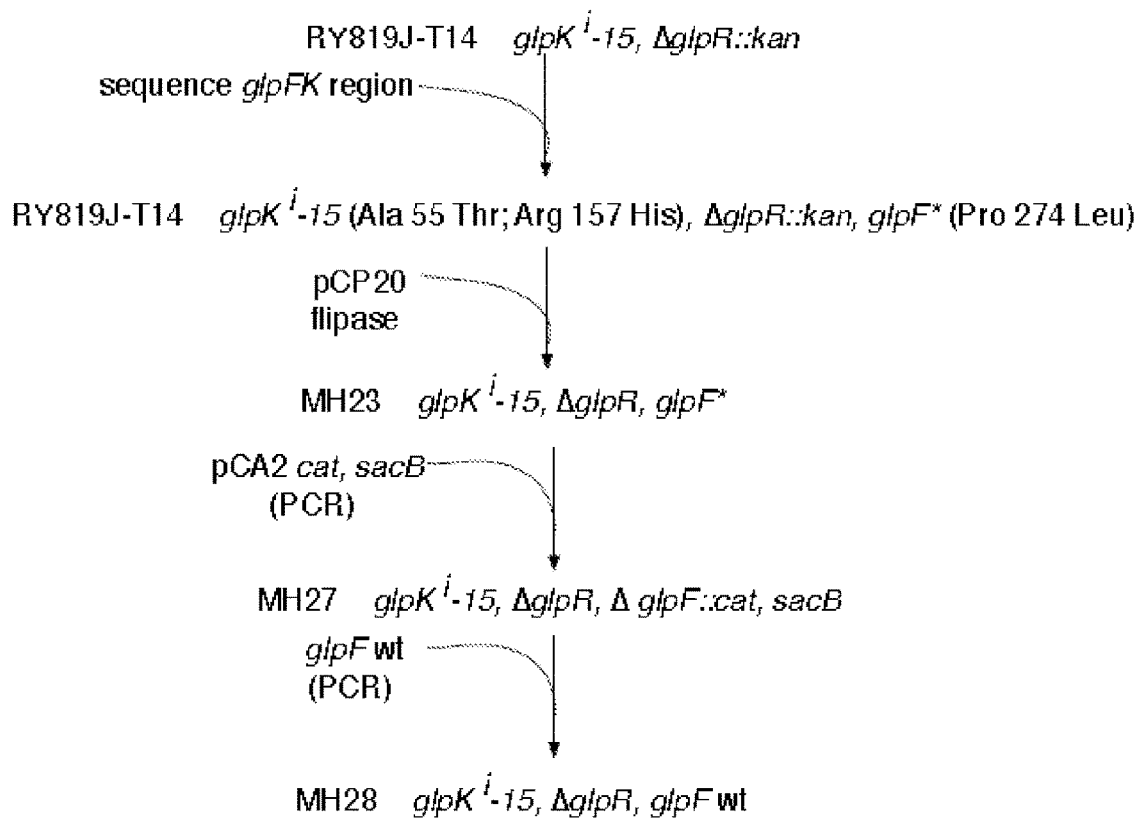
FIG. 3 Construction of glycerol utilizing E. coli strain MH28. DNA sequencing in the glpFK region of the RY819J-T14 strain of E. coli obtained at the end of metabolic evolution revealed two amino acid substitutions (Ala 55 Thr; Arg 157 His) within the open reading frame of glpK gene and one amino acid substitution (Pro 274 Leu) within the open reading frame of glpF gene. The mutation within glpF region was cured through a two-step process. In the first step, the glpF gene with the amino acid substitution (Pro 274 Leu) was inactivated with the insertion of a cat-sacB gene cartridge. In the next step, the cat-sacB gene cartridge was replaced by a wild type glpF gene sequence leading to the generation of MH28 strain of E. coli strain. The three mutations found in glpF and glpK were also found in the donor strain BB14-20.
Figure 4:
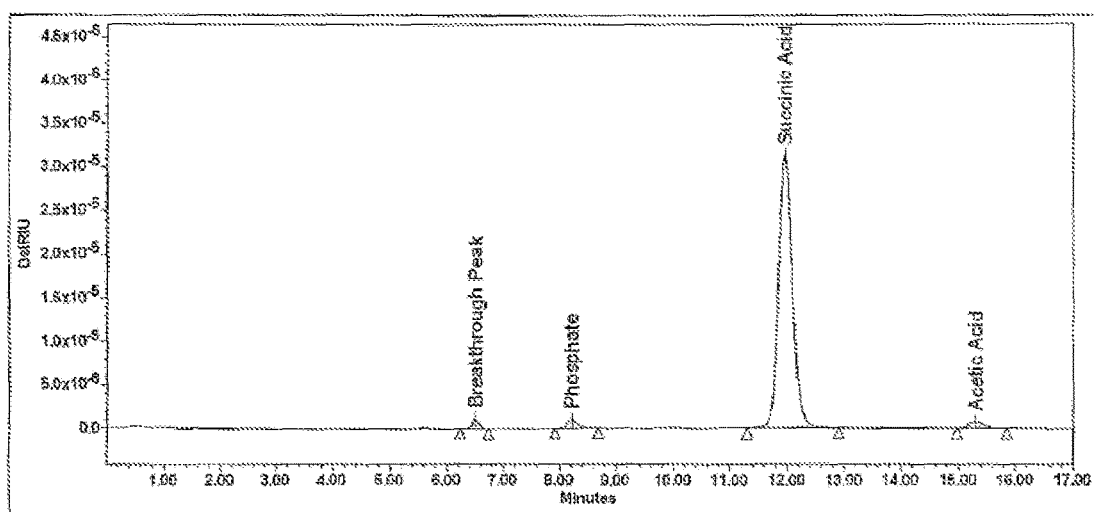
FIG. 4 A representative HPLC profile for a fermentation broth containing succinic acid. The fermentation broth obtained from the MH28 strain of E. coli strain grown in a medium containing nominally 10% (w/w) of glycerol was processed according to the procedure described in the specification. The processed sample was run on HPLC equipment fitted with a BioRad Aminex HPX-87H column (see Example 2).

A point mutation was found in the glpF gene of strain BB20-14, and because this mutation is closely linked to the glpK gene, it became installed in RY819J and passed down to strain MH23 (see Examples 1 and 5). The mutation in glpF was cured by replacing the region with a wild type DNA sequence, using the two step gene replacement method similar to that described by Jantama et al (2008a, 2008b). In the first step, a cat, sacB cassette was amplified by PCR using pCA2 (SEQ ID No. 11) as a template and primers BY71 (SEQ ID No. 6) and BY72 (SEQ ID No. 7). The resulting 3.2 kilobase DNA fragment was transformed into strain MH23 containing the helper plasmid pKD46 (Datsenko and Wanner, 2000), selecting for chloramphenicol resistance on LB plus 30 mg/l chloramphenicol, to give strain MH27 (glpF:: cat, sacB). For the second step, the wild type glpF region was amplified by PCR using E. coli C (ATCC 8739) DNA as template and primers BY73 (SEQ ID No. 8) and BY74 (SEQ ID No. 9). The resulting 1.7 kilobase DNA fragment was transformed into MH27, selecting for sucrose resistance on LB plus 6% sucrose, and confirming for chloramphenicol sensitivity on LB plus 30 mg/l chloramphenicol. The resulting strain, after curing of pKD46, was named MH28 (FIG. 3). The glpF and glpK region of MH28 was sequenced to confirm that the wild type glpF had been installed and that the feedback resistant mutations in glpK had been retained through the steps of strain construction.

Example 7

Figure 5:
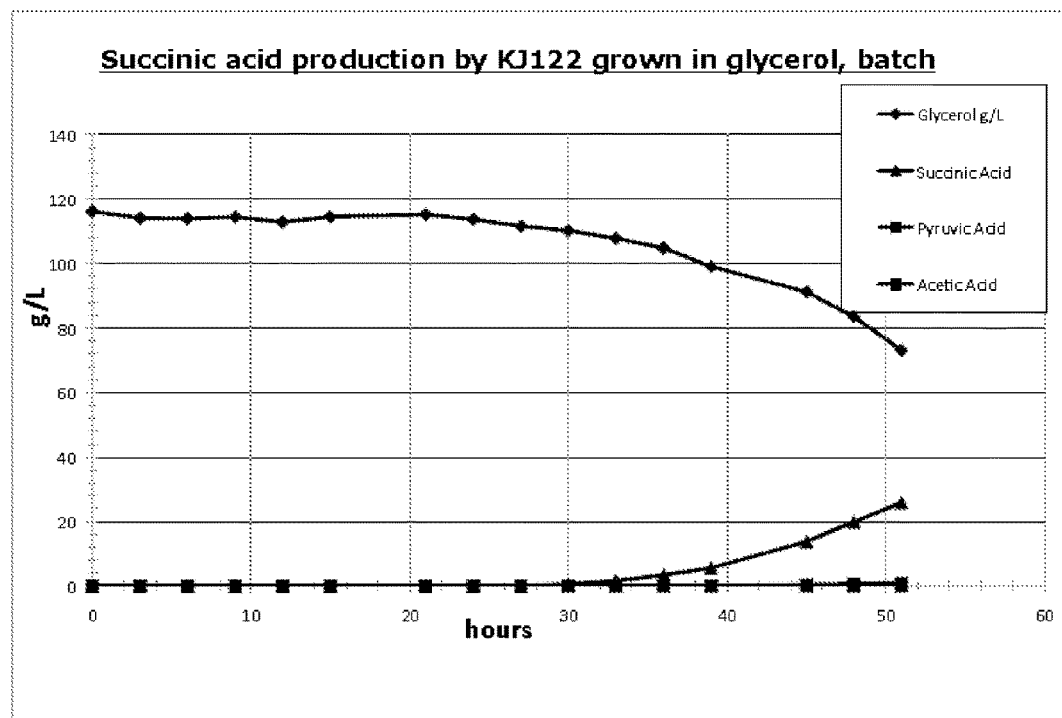
FIG. 5 Kinetics of glycerol utilization by the KJ122 strain of E. coli. The KJ122 strain was grown in a minimal medium with 10% (w/w) glycerol in a 7 L fermentor under microaerobic condition as described in the specification. The fermentor was run for a period of 52 hours and the glycerol consumption as well as the accumulation of succinic acid, pyruvic acid, and acetic acid were monitored using an HPLC apparatus as described in the specifications.
Figure 6:
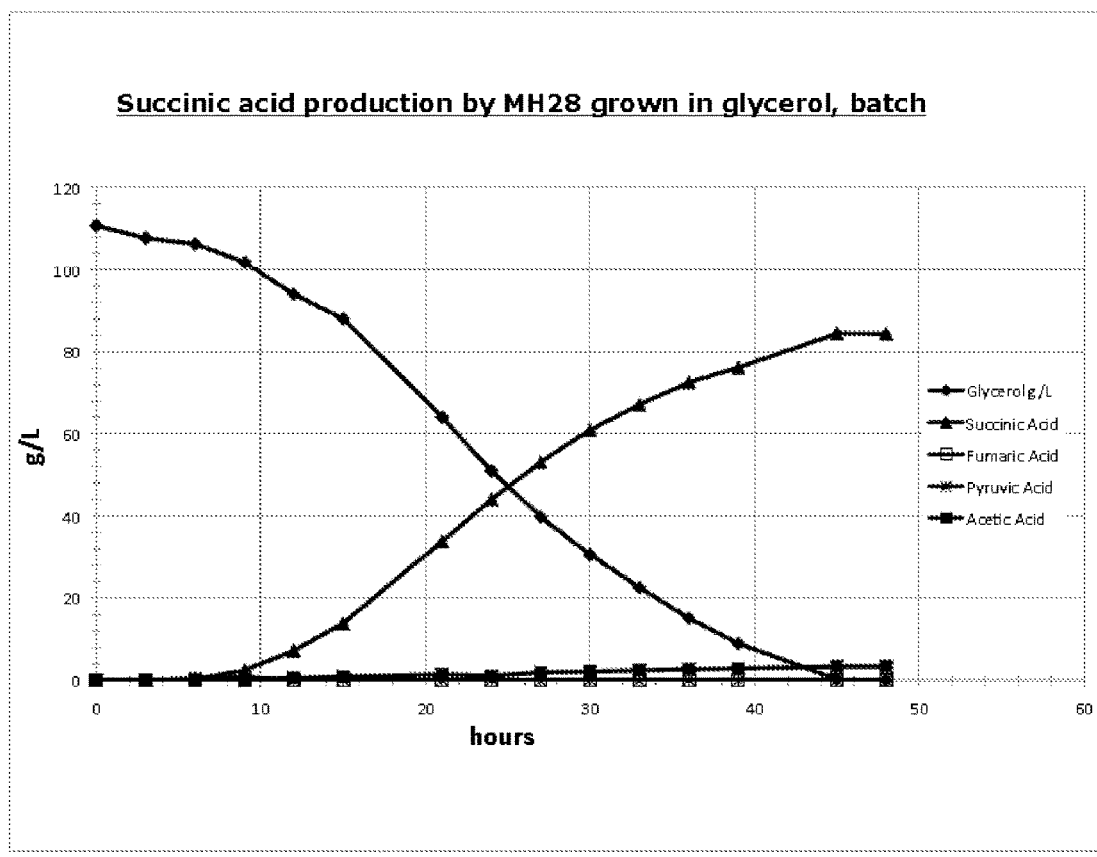
FIG. 6 Kinetics of glycerol utilization by the MH28 strain of E. coli. The MH28 strain was grown in a minimal medium with 10% (w/w) glycerol in a 7 L fermentor under microaerobic condition as described in the specification. The fermentor was run for a period of 52 hours and the glycerol consumption as well as the accumulation of succinic acid, fumaric acid, pyruvic acid, and acetic acid were monitored using an HPLC apparatus as described in the specifications.

Production of Succinate from Glycerol by KJ122 and MH28 in pH Controlled Fermentors Starting strain KJ122 and derivative strain MH28 were assessed for succinate production in 7 liter New Brunswick Scientific fermentors with a starting volume of 3.15 liters, including the inocula (FIGS. 5 and 6). The 150 ml inocula were grown aerobically in shake flasks overnight using NBS medium (see Table 1) containing 20 g/l glycerol and 0.1 M MOPS buffer, pH 7.0. The inocula were added to fermentors containing 3 liters of fermentation medium that nominally included 120 g/l glycerol (A.C.S. grade, Mallinckrodt Chemicals, catalog number 5092-02, CAS No. 56-81-5) as the sole carbon source (see Table 1). See Table 4 for the measured concentration of glycerol at time zero and the end of fermentation. The temperature was kept at 39° C., and the pH was kept at 7.0 by pumping in 3M potassium carbonate, as required. Microaeration was constant by pumping in air at 40 ml/min, which was shown to be sufficient for an attractive level of succinate production, by systematically varying the aeration rate. The impeller speed was 750 rpm.

Samples were taken and assayed for organic acids and glycerol using HPLC as described above. By 48 hours, the glycerol had been completely consumed by strain MH28, but not by parent strain KJ122 (see Table 4). MH28 produced 84.3 g/l succinate, for a yield of 1.0 g/g glycerol consumed. The only significant byproduct was acetate at 3.3 g/l. In contrast, KJ122, the starting strain, made only 18.9 g/l succinate and left 83.5 g/l glycerol in the final broth at 48 hours, for a succinate yield of 0.6 g/g glycerol consumed. Clearly, strain MH28 is much improved over strain KJ122 for succinate production under the conditions tested.

A scientist skilled in the art would be able use the methods described herein to construct strains similar to MH28, but containing other alleles of the glpK gene that encode feedback resistant glycerol kinase. Several possible alleles were mentioned above, including the glpK$^i$14, glpK$^i$22, and glpK$^i$31 alleles, as well as alleles described by Honisch et al. (2004). For example mutations causing the following amino acid changes in glycerol kinase: Gln28Pro, Trp54Gly, Val62Leu, Asp73Ala, Asp73Val, Gly231Asp, and the insertion of 235GlyGlyLys can be used to confer feedback resistant phenotype.

A scientist skilled in the art would also recognize that the methods disclosed herein could be used to construct strains that ferment glycerol to other organic acids of commercial interest, such as lactate, malate, and fumarate.

Although the specific examples given in this specification used *E. coli* as a production organism, and the genes used in the examples use the *E. coli* nomenclature (for example glpR (glycerol-3-phosphate dependent repressor), glpK (glycerol kinase), glpABC (glycerol-3-phosphate dehydrogenase), and glpF (glycerol facilitated diffuser)), one skilled in the art will know that genes and proteins that are functional analogs and structural homologs of these components from other microorganisms can be engineered as taught in this specification to achieve enhanced utilization of glycerol for production of chemicals of commercial interest by fermentation in other microorganisms.

REFERENCES

All references are listed herein for the convenience of the reader. Each is incorporated by its entirety.

U.S. Pat. No. 5,000,000
U.S. Pat. No. 5,028,539
U.S. Pat. No. 5,424,202
U.S. Pat. No. 5,482,846
U.S. Pat. No. 5,916,787
U.S. Pat. No. 6,849,439
U.S. Pat. No. 7,098,009
U.S. Pat. No. 7,223,567
U.S. Pat. No. 7,241,594
U.S. Pat. No. 7,244,610
U.S. Pat. No. 7,262,046
U.S. Pat. No. 7,470,530
U.S. Pat. No. 7,629,162
U.S. Pat. No. 7,790,416
United States Patent Application Publication No. US 2009/0176285
United States Patent Application Publication No. US 2009/0186392
United States Patent Application Publication No. US 2009/0148914
United States Patent Application Publication No. US 2010/0184171
United States Patent Application Publication No. US 2011/0008851
International Patent Application Publication No. WO/2007/115228
International Patent Application Publication No. WO 2008/115958
International Patent Application Publication No. WO 2009/024294
International Patent Application Publication No. WO 2009/048202
International Patent Application Publication No. WO 2010/051324
International Patent Application Publication No. WO 2010/092155
International Patent Application Publication No. WO 2010/115067
Baba, T., Ara, T., Hasegawa, M., Takai, Y., Okumura, Y., Baba, M., Datsenko, K. A., Tomita, M., Wanner, B. L., and Mori, H. (2006) Construction of *Escherichia coli* K-12 in-frame, single-gene knockout mutants: the Keio collection. *Mol Syst Biol* 2: 2006 0008.
Bell, R. M. (1974) Mutants of *Escherichia coli* defective in membrane phospholipid synthesis: macromolecular synthesis in an sn-glycerol 3-phosphate acyltransferase Km mutant. *J Bacteriol* 117: 1065-1076.
Berman, M., and Lin, E. C. (1971) Glycerol-specific revertants of a phosphoenolpyruvate phosphotransferase mutant: suppression by the desensitization of glycerol kinase to feedback inhibition, *J Bacteriol* 105: 113-120.
Blankschien, M. D., Clomburg, J. M., and Gonzalez, R. (2010) Metabolic engineering of *Escherichia coli* for the production of succinate from glycerol. *Metab Eng* 12: 409-419.
Chen, Z., Liu, H., Zhang, J., and Liu, D. (2010) Elementary mode analysis for the rational design of efficient succinate conversion from glycerol by *Escherichia coli*. *J Biomed Biotechnol* 2010: 518743.
Clomburg, J. M., and Gonzalez, R. (2010) Biofuel production in *Escherichia coli*: the role of metabolic engineering and synthetic biology. *Appl Microbiol Biotechnol* 86: 419-434.
Clomburg, J. M., Gonjalez, R. (2010) Metabolic Engineering of *Escherichia coli* for the production of 1,2-propanediol from glycerol. *Biotech. Bioeng.*: 108: 867-879.
Cronan, J. E., Jr., and Bell, R. M. (1974a) Mutants of *Escherichia coli* defective in membrane phospholipid synthesis: mapping of the structural gene for L-glycerol 3-phosphate dehydrogenase. *J Bacteriol* 118: 598-605.
Cronan, J. E., Jr., and Bell, R. M. (1974b) Mutants of *Escherichia coli* defective in membrane phospholipid synthesis: mapping of sn-glycerol 3-phosphate acyltransferase Km mutants. *J Bacteriol* 120:227-233.
Datsenko, K. A., and Wanner, B. L. (2000) One-step inactivation of chromosomal genes in *Escherichia coli* K-12 using PCR products. *Proc Natl Acad Sci USA* 97: 6640-6645.
De Guzman, D. (2010) ICIS Chemical Business, Volume 18, p. 48

Durnin, G., Clomburg, J., Yeates, Z., Alvarez, P. J., Zygourakis, K., Campbell, P., and Gonzalez, R. (2009) Understanding and harnessing the microaerobic metabolism of glycerol in *Escherichia coli*. *Biotechnol Bioeng* 103: 148-161.

Gonzalez, R., Murarka, A., Dharmadi, Y., and Yazdani, S. S. (2008) A new model for the anaerobic fermentation of glycerol in enteric bacteria: trunk and auxiliary pathways in *Escherichia coli*. *Metab Eng* 10: 234-245.

Herring, C. D., Raghunathan, A., Honisch, C., Patel, T., Applebee, M. K., Joyce, A. R., Albert, T. J., Blattner, F. R., van den Boom, D., Cantor, C. R., and Palsson, B. O. (2006) Comparative genome sequencing of *Escherichia coli* allows observation of bacterial evolution on a laboratory timescale. *Nat Genet*. 38: 1406-1412.

Honisch, C., Raghunathan, A., Cantor, C. R., Palsson, B. O., and van den Boom, D. (2004) High-throughput mutation detection underlying adaptive evolution of *Escherichia coli*-K12. *Genome Res* 14: 2495-2502.

Jantama, K., Haupt, M. J., Svoronos, S. A., Zhang, X., Moore, J. C., Shanmugam, K. T., and Ingram, L. O. (2008) Combining metabolic engineering and metabolic evolution to develop nonrecombinant strains of *Escherichia coli* C that produce succinate and malate. *Biotechnol Bioeng* 99: 1140-1153.

Jantama, K., Zhang, X., Moore, J. C., Shanmugam, K. T., Svoronos, S. A., and Ingram, L. O. (2008) Eliminating side products and increasing succinate yields in engineered strains of *Escherichia coli* C. *Biotechnol Bioeng* 101: 881-893.

Ibarra, R. U., Edwards, J. S., and Palsson, B. O. (2002) *Escherichia coli* K-12 undergoes adaptive evolution to achieve in silico predicted optimal growth. *Nature* 420: 186-189.

Lin, E. C. (1996), in *Escherichia coli and Salmonella: cellular and molecular biology*, 2nd ed., ASM Press, Washington, D.C., pp 325-326.

Ondrey, G. (2004) Chemical Engineering, October, 2004, p. 13).

Palsson, B. O. (2011) Adaptive Laboratory Evolution, Microbe 6, 69-74.

Pettigrew, D. W., Liu, W. Z., Holmes, C., Meadow, N. D., and Roseman, S. (1996) A single amino acid change in *Escherichia coli* glycerol kinase abolishes glucose control of glycerol utilization in vivo. *J Bacteriol* 178. 2846-2852.

Trinh, C. T., and Srienc, F. (2009) Metabolic engineering of *Escherichia coli* for efficient conversion of glycerol to ethanol. *Appl Environ Microbiol* 75. 6696-6705.

Yazdani, S. S., and Gonzalez, R. (2007) Anaerobic fermentation of glycerol: a path to economic viability for the biofuels industry. *Curr Opin Biotechnol* 18: 213-219.

Yazdani, S., and Gonzalez, R. (2008) Engineering *Escherichia coli* for the efficient conversion of glycerol to ethanol and co-products. *Metabolic Engineering* 10: 340-351.

Zhang, X., Jantama, K., Moore, J. C., Jarboe, L. R., Shanmugam, K. T., and Ingram, L. O. (2009) Metabolic evolution of energy-conserving pathways for succinate production in *Escherichia coli*. *Proc Natl Acad Sci USA* 106: 20180-20185.

Zhang, X., Jantama, K., Shanmugam, K. T., and Ingram, L. O. (2009) Reengineering *Escherichia coli* for Succinate Production in Mineral Salts Medium. *Appl Environ Microbiol* 75: 7807-7813.

Zhang, X., Shanmugam, K. T., and Ingram, L. O. (2010) Fermentation of glycerol to succinate by metabolically engineered strains of *Escherichia coli*. *Appl Environ Microbiol* 76:2397-2401.

Zwaig, N., and Lin, E. C. (1966) Feedback inhibition of glycerol kinase, a catabolic enzyme in *Escherichia coli*. *Science* 153: 755-757.

Zwaig, N., Kistler, W. S., and Lin, E. C. (1970) Glycerol kinase, the pacemaker for the dissimilation of glycerol in *Escherichia coli*. *J Bacteriol* 102: 753-759.

TABLE 1

Chemical composition of minimal media used in the present invention. The final pH was adjusted to 7.0 with ammonia or phosphoric acid as needed

| Ingredient | Spizizen Salts (SS) | New Brunswick Scientific (NBS) | AM1 | Fermentation medium | 1000 X Trace Elements |
|---|---|---|---|---|---|
| $KH_2PO_4$ | 6.0 g/l | 3.5 g/l | | | |
| $K_2HPO_4$ | | 5.0 g/l | | | |
| $K_2HPO_4 \cdot 3H_2O$ | 17.4 g/l | | | | |
| $(NH_4)_2HPO_4$ | | 3.5 g/l | 2.63 g/l | 2.63 g/l | |
| $(NH_4)H_2PO_4$ | | | 0.87 g/l | 0.87 g/l | |
| $MgSO_4$ | 0.2 g/l | 1 mM | 1.5 mM | 2.0 mM | |
| $CaCl_2$ | 0.1 mM | 0.1 mM | 0.1 mM | | |
| $(NH_4)_2SO4$ | 2 g/l | | | | |
| $Na_3Citrate$ | 10 g/l | | | | |
| $KHCO_3$ | | 0-100 mM | 0-30 mM | | |
| KCl | | | 2 mM | | |
| Betaine | | | 1 mM | 1.33 mM | |
| Glucose | | 0-100 g/l | 0-100 g/l | | |
| Glycerol | | 10-100 g/l | 20-100 g/l | 100-120 g/l | |
| 1000 X trace elements | 1 ml/l | 1 ml/l | 1 ml/l | 3.3 ml/l | |
| MOPS buffer | | 0.1M, pH 7.4 | | | |
| Antifoam 204 | | | | 8 ppm | |
| $FeCl_3$ | | | | | 1.6 g/l |
| $CoCl_2 \cdot 6H_2O$ | | | | | 0.2 g/l |
| $CuCl_2$ | | | | | 0.1 g/l |
| $ZnCl_2 \cdot 4H_2O$ | | | | | 0.2 g/l |
| $NaMoO_4$ | | | | | 0.2 g/l |
| $H_3BO_3$ | | | | | 0.05 g/l |
| $MnCl_2 \cdot 4H_2O$ | | | | | 0.55 g/l |
| HCl | | | | | 0.1M |

TABLE 2

Metabolic evolution of PY819J. All transfers started with 50 g/l glycerol. Glucose was added either at the start or at a later time period as indicated below.

| Transfer number | Amount of glucose added at the start of fermentation (g/l) | Amount of glucose added as a supplement at a later time period (g/l) | Time period at which the supplemental glucose was added (hours from the start of the fermentation) | Neutralizing base* | Total duration of the fermentation before next transfer |
|---|---|---|---|---|---|
| 1 | 50 | none | | a | 72 |
| 2 | 50 | none | | a | 71 |
| 3 | 50 | none | | a | 71 |
| 4 | 50 | none | | a | 74 |
| 5 | 0 | 10 g/l glucose | 49 | b | 145 |
| 6 | 0 | 10 g/l glucose | 48 | b | 97 |
| 7 | 0 | 10 g/l glucose | 72 | b | 96 |
| 8 | 0 | 10 g/l glucose | 165 | b | 214 |
| 9 | 0 | 10 g/l glucose | 239 | b | 288 |
| 10 | 0 | 1 g/l KNO$_3$<br>10 g/l glucose | 120<br>142 | b | 216 |
| 11 | 0 | none | | b | 98 |
| 11a | 0 | none | | b | 413 |
| 13 | 0 | none | | b | 211 |
| 14 | 0 | none | | b | |

*Neutralizing bases were a: 1.2M KOH + 2.4M K$_2$CO$_3$; b: 3M K$_2$CO$_3$

TABLE 3

Primer sequences and bacterial plasmids

Primers

| Primer No./Primer name | Primer sequence |
|---|---|
| SEQ ID No. 1/BY19 | 5' tccggcgcgccaccaatac 3' |
| SEQ ID No. 2/BY44 | 5' cagtgtcatttggggactggggg 3' |
| SEQ ID No. 3/BY15 | 5' gtatacggtcagactaacattggcggc 3' |
| SEQ ID No. 4/BY16 | 5' cgccagtgttcatcagcataaagcag 3' |
| SEQ ID No. 5/BY30 | 5' atcagctttcgccagcacttctaccagc 3' |
| SEQ ID No. 6/BY71 | 5'acttttgcttccagtttctcaaacacttctaatgacattgtcatacctctgtgacg gaagatcacttcgcagaata 3' |
| SEQ ID No. 7/BY72 | 5'acgatatatttttttcagtcatgtttaattgtcccgtagtcatattacatgaagca cttcactgacaccctcatc 3' |
| SEQ ID No. 8/BY73 | 5'caacctggttttgggtagatttgctc3' |
| SEQ ID No. 9/BY74 | 5'acagtaaagaaattacgcggaagatgaag3' |

Bacterial Plasmids

| SEQ ID No./Plasmid Name | Description |
|---|---|
| SEQ ID No. 10/pRY521 | Parent of pMH4 series |
| SEQ ID No. 11/pCA2 | Source of cat, sacB cassette |

TABLE 4

Production of succinate from glycerol by KJ122 and MH28

| Strain | Starting glycerol | Time | Succinate titer | Remaining glycerol | Acetate titer | Succinate yield g/g | OD at 550 nm |
|---|---|---|---|---|---|---|---|
| KJ122 | 116 g/l | 48 hr | 19.8 g/l | 83.5 g/l | 0.6 g/l | 0.6 | 7.6 |
| MH28 | 111 g/l | 48 hr | 84.3 g/l | 0 g/l | 3.3 g/l | 1.0 | 8.0 |

What is claimed is:

1. A genetically engineered *Escherichia coli* bacterium, comprising a mutated glpK gene that encodes a feedback resistant glycerol kinase and a mutated glpR gene that exhibits decreased activity as a repressor of one or more glycerol utilization genes selected from the group consisting of glpFKX operon, glpABC operon, and glpD gene, wherein said genetically engineered *Escherichia coli* bacterium is capable of producing succinic acid from glycerol in a minimal medium with a titer of at least 20 g/L and a yield of at least 0.6 in less than 48 hours.

2. The genetically engineered *Escherichia coli* bacterium of claim 1, wherein said feedback resistant glycerol kinase is resistant to inhibition by fructose-1,6-bisphosphate.

3. The genetically engineered *Escherichia coli* bacterium of claim 1, wherein said feedback resistant glycerol kinase is resistant to inhibition by non-phosphorylated Enzyme IIA$^{Glc}$ of a phosphotransferase system.

4. A method for producing succinic acid, comprising:
(a) growing said genetically engineered *Escherichia coli* bacterium of claim 1 in a fermentor comprising a minimal medium and glycerol for less than 48 hours, wherein said genetically engineered *Escherichia coli* bacterium produces succinic acid from said glycerol with a titer of at least 20 g/L and a yield of at least 0.6; and
(b) harvesting said succinic acid from said fermentor.

5. The method of claim 4, wherein said fermentor is aerated at a rate that provides less than 0.15 liters of oxygen per liter of broth per minute.

6. The method of claim 4, wherein said fermentor is aerated at a rate provides more than 20 milligrams of oxygen per liter of broth per hour.

7. The method of claim 4, wherein said fermentor is aerated at a rate that provides less than 0.15 liters of oxygen per liter of broth per minute and more than 20 milligrams of oxygen per liter of broth per hour.

* * * * *